United States Patent
Schabbach et al.

(10) Patent No.: US 11,504,473 B2
(45) Date of Patent: Nov. 22, 2022

(54) MIXING AND/OR RECONSTITUTION SYSTEM AND RESPECTIVE METHOD

(71) Applicant: SANOFI, Paris (FR)

(72) Inventors: Michael Schabbach, Frankfurt am Main (DE); Dieter Kadereit, Frankfurt am Main (DE); Andrea Heiberger, Frankfurt am Main (DE); Claus Geiger, Frankfurt am Main (DE); Charlotte Emma Harvey, Harston (GB); Congyi Huang, Cambridge (GB); Timothy Charles Frearson, Harston (GB); Alexander David Norman, Harston (GB)

(73) Assignees: Sanofi, Paris (FR); Sagentia Ltd., Cambridge (GB)

( * ) Notice: Subject to any disclaimer, the term of this patent is extended or adjusted under 35 U.S.C. 154(b) by 287 days.

(21) Appl. No.: 16/763,282

(22) PCT Filed: Nov. 15, 2018

(86) PCT No.: PCT/EP2018/081386
§ 371 (c)(1),
(2) Date: May 12, 2020

(87) PCT Pub. No.: WO2019/096913
PCT Pub. Date: May 23, 2019

(65) Prior Publication Data
US 2020/0330686 A1    Oct. 22, 2020

(30) Foreign Application Priority Data
Nov. 17, 2017    (EP) .................................... 17306599

(51) Int. Cl.
*A61M 5/19* (2006.01)
*A61M 5/315* (2006.01)
*A61J 1/20* (2006.01)

(52) U.S. Cl.
CPC .............. *A61M 5/19* (2013.01); *A61J 1/2086* (2015.05); *A61J 1/2096* (2013.01); *A61M 5/31596* (2013.01); *A61M 2205/0272* (2013.01)

(58) Field of Classification Search
CPC .. A61M 2005/2013; A61M 2005/2474; A61M 2005/3128; A61M 2005/31598;
(Continued)

(56) References Cited

U.S. PATENT DOCUMENTS 4,968,299 A * 11/1990 Ahlstrand ........... A61M 5/2448
D24/114
5,360,410 A * 11/1994 Wacks ................. A61M 5/322
604/206
(Continued)

FOREIGN PATENT DOCUMENTS

| CN | 201290957 | 8/2009 |
|---|---|---|
| CN | 102671264 | 9/2012 |

(Continued)

OTHER PUBLICATIONS

International Search Report and Written Opinion in Application No. PCT/EP2018/081386, dated Jan. 3, 2019, 11 pages.
(Continued)

*Primary Examiner* — Quynh-Nhu H. Vu
(74) *Attorney, Agent, or Firm* — Fish & Richardson P.C.

(57) ABSTRACT

A mixing and/or reconstitution system reduces the possibility of user error and provides a well mixed and/or reconstituted drug in a short time. The system comprises a device containing a first material within a first chamber, a housing, (Continued)

and a plunger, the plunger comprising a second chamber containing a second material, wherein one of the first and the second material is a fluid, and a movable element with an electric, magnetic, or paramagnetic characteristic, wherein the second chamber is initially closed; and a base unit comprising a recess for accommodation of the device, a control unit, and an electromagnetic unit which is adapted to produce an electromagnetic field penetrating the recess, wherein the control unit can electrically operate the electromagnetic unit such that the element contained in the second chamber moves in a direction of the device determined by the electromagnetic field and fluidly communicates the first and second chambers.

20 Claims, 22 Drawing Sheets

(58) Field of Classification Search
CPC .. A61M 2005/3267; A61M 2205/0272; A61M 2209/04; A61M 5/1782; A61M 5/19; A61M 5/20; A61M 5/2053; A61M 5/2066; A61M 5/2448; A61M 5/31596; A61M 5/445; A61J 1/2086; A61J 1/2096
See application file for complete search history.

(56) References Cited

U.S. PATENT DOCUMENTS

| | | | |
|---|---|---|---|
| 2011/0082388 A1* | 4/2011 | Hunter | A61B 10/02 600/573 |
| 2011/0092906 A1 | 4/2011 | Boettger et al. | |
| 2012/0136298 A1* | 5/2012 | Bendix | A61M 5/31515 29/428 |
| 2013/0296807 A1 | 11/2013 | Lintern et al. | |
| 2014/0088486 A1 | 3/2014 | Uhland et al. | |
| 2016/0008779 A1 | 1/2016 | Seaward et al. | |

FOREIGN PATENT DOCUMENTS

| | | |
|---|---|---|
| CN | 102698342 | 10/2012 |
| JP | H07-501234 | 2/1995 |
| WO | WO 93/02720 | 2/1993 |
| WO | WO 98/33538 | 8/1998 |
| WO | WO 99/17820 | 4/1999 |
| WO | WO 2016/061548 | 4/2016 |

OTHER PUBLICATIONS

International Preliminary Report on Patentability in Application No. PCT/EP2018/081386, dated May 19, 2020, 8 pages.

* cited by examiner

MIXING AND/OR RECONSTITUTION SYSTEM AND RESPECTIVE METHOD

CROSS REFERENCE TO RELATED APPLICATIONS

The present application is the national stage entry of International Patent Application No. PCT/EP2018/081386, filed on Nov. 15, 2018, and claims priority to Application No. EP 17306599.6, filed on Nov. 17, 2017, the disclosures of which are incorporated herein by reference.

TECHNICAL FIELD

The disclosure refers to a mixing and/or reconstitution system, in particular a drug mixing and/or reconstitution system, a respective device, and a respective mixing and/or reconstitution method.

BACKGROUND

Certain drugs are ideally administered in a liquid form, injected subcutaneously for the optimal therapeutic effect. However, some of these liquid drugs are unstable, having a shelf live that is relatively short. This can be a problem both for prophylactic treatments, where patients must inject themselves on a regular basis and therefore want to keep a reasonable supply of drug at home, and for emergency treatments, where patients need to keep a supply of the drug to hand but may not need it for weeks or longer.

SUMMARY

In this case often drugs in a concentrated liquid form or lyophilized (freeze-dried) drugs are used, which usually comprise separate components, namely a powder or liquid which is much more stable and therefore has a long shelf life, and a diluent liquid. These components are typically supplied in separate vials and the user must reconstitute the drug prior to injection. Such reconstitution is often a complex process with many steps. Also, there is the risk during the reconstitution process at various points that, if the user is not careful, the drug can be contaminated. Therefore, there is a need for a system and a method which removes the possibility of user error and provides a well mixed and/or reconstituted drug in a short time.

From document US 2013/0296807 A1 a device for automatic reconstitution and delivering a drug to a user and a method thereof is known. There is a need for a system or injection device which reduces the possibility of user error and provides an easy and automatic operation.

The above problem is solved by the device defined in claim 1. It is further solved by the system defined in claim 6 and the method defined in claim 11.

In particular, the inventive mixing and/or reconstitution system comprises a device containing a first material within a first chamber, a housing and a plunger, wherein the plunger comprises a second chamber, e.g. within the plunger rod, for example at its distal end, containing a second material, wherein one of the first and the second material is a fluid, and a movable element (i.e. the movable element is contained within the second chamber) with an electric, magnetic or paramagnetic characteristic, wherein the second chamber is initially closed, a base unit comprising an recess for accommodation of the device, a control unit, and an electromagnetic unit which is adapted to produce an electromagnetic field penetrating the recess, wherein the control unit electrically operates the electromagnetic unit, wherein the base unit is adapted such that after accommodation of the device within the recess and after user activation of the base unit the control unit operates the electromagnetic unit such that the element contained in the second chamber moves in a (pre-determined) direction of the device determined by the electromagnetic field and thereby opens a path providing a fluid communication between the first chamber and the second chamber. For that purpose, the electromagnetic field may accelerate the element (which may be initially in a rest position within the second chamber) by an axial force (the term "axial" refers to the longitudinal axis of the device) into a pre-determined direction to a pre-determined velocity (such that the element exerts sufficient force) such that it opens the fluid communication path.

The present disclosure particularly refers to the mixing and/or reconstitution of a first drug component formed by or contained within the first material and a second drug component formed by or contained within the second material. Reconstitution is the rehydration of a lyophilized (freeze dried) drug (e.g. first drug component) by a diluent (e.g. second drug component). The term mixing refers to any other intermixing of any first and second drug component.

The advantage of the inventive system consists therein that the system is extremely user convenient because the user has only to place the medical device within the recess of the base unit, activate the base unit and wait until mixing and/or reconstitution is complete which occurs after the fluid communication between the first chamber and the second chamber is established. This may be visually checked by the user. The inventive system removes the possibility of user error. After user activation the mixing and/or reconstitution process is provided fully automatically. It is also easy to use, fast and low cost.

In one embodiment the device is a cartridge, a syringe or an autoinjector. In another embodiment the base unit is a disposable device. Further, the device may be pre-filled, in particular its first and second chamber. The device may contain the first drug component in a cartridge, in case it is a syringe or an autoinjector. The first material may be a fluid drug component, for example a diluent, and the second material may be formed by a fluid and/or solid drug component, for example a lyophilized drug.

In one embodiment the distal end of the second chamber, which may be formed as a cylinder, is covered by a seal, which may be formed as a foil or another material, for example comprising or consisting of an aluminium-polymer laminate or a low-permeability polymer such as a cyclic olefin.

In one embodiment the recess has a cylindrical form or the form of a section of the cylinder and the movement of the element is along the axial direction of the cylinder. Further, the device may comprise a needle which is attached at its distal end, preferably covered by a needle cover. Further, the electromagnetic unit may be provided in the vicinity of the recess.

The user activation may be provided by pressing an on/off button, switching on via remote control and/or setting a timer with a pre-defined time point.

The opening of the communication path between the first chamber and the second chamber is, for example, facilitated by puncturing a seal covering the distal end of the second chamber by the element contained in the second chamber caused by a distal movement of the element thereby allowing the first material and the second material to mix and/or reconstitute within the first chamber and/or the second chamber.

The slug-like element may comprise sintered Neodymium-Iron-Boron (NdFeB), preferably with a medical-grade coating, Samarium-Cobalt (SmCo) and Aluminium-Nickel-Cobalt (AlNiCo). The middle or main section of the element slug-like may be formed as a cylinder. Alternatively, it may have a shape of a barrel or of a section of a sphere. One distal end of this element may be shaped as a sharp tip to puncture a seal that prevents communication between the first chamber and the second chamber. Additionally, the proximal end of the element may be tapered in order to help the element to slide back up into the plunger.

In another embodiment the electromagnetic unit of the base unit comprises at least one electromagnetic coil surrounding the recess for the device. Additionally, the recess of the base station may contain a sensor (e.g. proximity sensor) for the device recognizing the correct and full insertion of the device within the recess. In case the sensor does not notice a device correctly inserted within the recess a mixing and/or reconstitution step is prevented.

Further the electromagnetic unit may comprise a series of electromagnetic coils and mild steel pole pieces in between two adjacent electromagnetic coils.

In another embodiment the control unit is adapted to energize one electromagnetic coil or electromagnetic coils of the electromagnetic unit such that the produced electromagnetic field moves the element along a pre-defined direction of the device back and forth.

For example, the system may comprise four electromagnetic coils, wherein the four coils accommodated side by side along the axial direction, wherein at any one time, two coils are active alternating with the other two coils, the two active coils are energized in opposite directions, and interact with the two magnetic poles of the element to generate an axial force such that, in one step, one coil repels one magnetic pole of the element and the other coil of the two active coils attracts the other magnetic pole of the element.

In one embodiment the movement of the element, for example after opening of the path providing a fluid communication is within the first and/or the second chamber.

In one embodiment the electromagnetic unit comprises at least one permanent magnet which is moveable along a pre-defined direction of the device.

In one embodiment the base station comprises a separate interlock system holding the device within the recess of the base station until mixing is complete. In one embodiment the device is held stationary (i.e. does not move) after activation during mixing and/or reconstituting of the first and second material. In one embodiment the plunger is held stationary (i.e. does not move) after activation during mixing and/or reconstituting of the first and second material.

In another embodiment the electromagnetic unit is adapted such that it produces an electromagnetic field after activation, for example a highly concentrated electromagnetic field after activation.

The inventive device contains a first material within a first chamber, a housing and a plunger, wherein the plunger comprises a second chamber containing a second material, wherein one of the first and the second material is a fluid, and a movable element with an electric, magnetic or paramagnetic characteristic, wherein the second chamber is initially closed, wherein the element, the first chamber and the second chamber are adapted such that after activation by an electromagnetic field the element moves in a pre-determined direction of the device relative to the (stationary) device or relative to the (stationary) plunger and thereby opens a path providing a fluid communication between the first chamber and the second chamber.

In one embodiment the element is a slug-like element and comprises a tip at its distal end and/or a tapered face at its proximal end.

Further, the element may comprise a permanent magnetic material, and preferably comprises a medical-grade coating, or comprises soft magnetic material, preferably mild steel or medical-grade stainless steel.

In another embodiment the device comprises a filter at the distal end of the first chamber and/or the seal is adapted such that it does not produce a shard, e.g. a small shard, when punctured or ruptured by the slug-like element.

Further the plunger may comprises a plate-like element comprising a soft magnetic material accommodated proximally with regard to the second chamber in order to hold the paramagnetic or magnetic element in place until the device is placed in the base station and activated. In an alternative embodiment instead of a plate like element a separate element may be used which the user has to remove is dislodged on insertion of the device in the base station. For example, the element may be a steel collar piece accommodated around the outside of housing of the device, which is slid away on insertion into base station.

Embodiments further comprise a mixing and/or reconstitution method comprising the following steps accommodating a device within an recess of a base unit, wherein the device contains a first material within a first chamber, a housing and a plunger, wherein the plunger comprises a second chamber containing a second material, wherein one of the first and the second material is a fluid, and a movable element with an electric, magnetic or paramagnetic characteristic, wherein the second chamber is initially closed, wherein the base unit comprises an electromagnetic unit which is adapted to produce an electromagnetic field penetrating the recess, and operating the electromagnetic unit by the control unit after activation such that the element contained in the second chamber of the device moves in a direction of the device determined by the electromagnetic field and thereby opens a path providing a fluid communication between the first chamber and the second chamber.

In one embodiment the electromagnetic unit is operated such that the produced electromagnetic field moves the element along a pre-defined direction of the device back and forth within the first chamber and/or the second chamber and/or the communication path. The electromagnetic unit may produce a highly concentrated and/or alternating and/or varying electromagnetic field for the movement of the element in order to effect mixing and/or reconstitution. For example, different coils in different directions and at different times are energized thereby causing the element to move backwards and forwards, for example in the axial (longitudinal) direction of the device within a pre-determined time period or over a pre-defined number of cycles.

In another embodiment the electromagnetic unit is operated such that at least one permanent magnet of the electromagnetic unit moves along a pre-defined direction of the device after activation.

In another embodiment at the end of the process, the element rests in a position within the previous second chamber of the plunger whereby it does not hinder injection.

As indicated above, the element may have a tapered proximal end to help it re-enter the plunger.

BRIEF DESCRIPTION OF FIGURES

Embodiments will now be described in further detail with reference to the accompanying schematic drawings, wherein.

DETAILED DESCRIPTION

Figure 1:
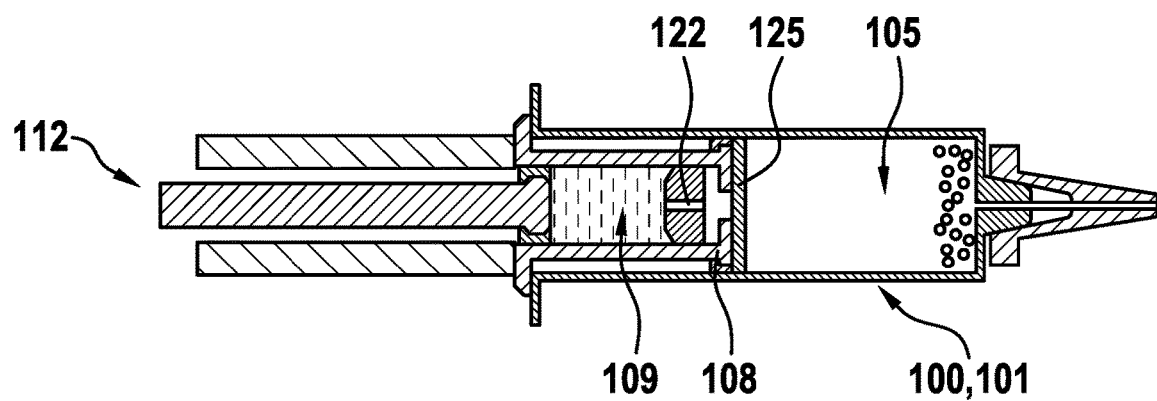
FIG. 1 shows a concept sketch of a first embodiment of an injection device in a sectional view.
Figure 2:
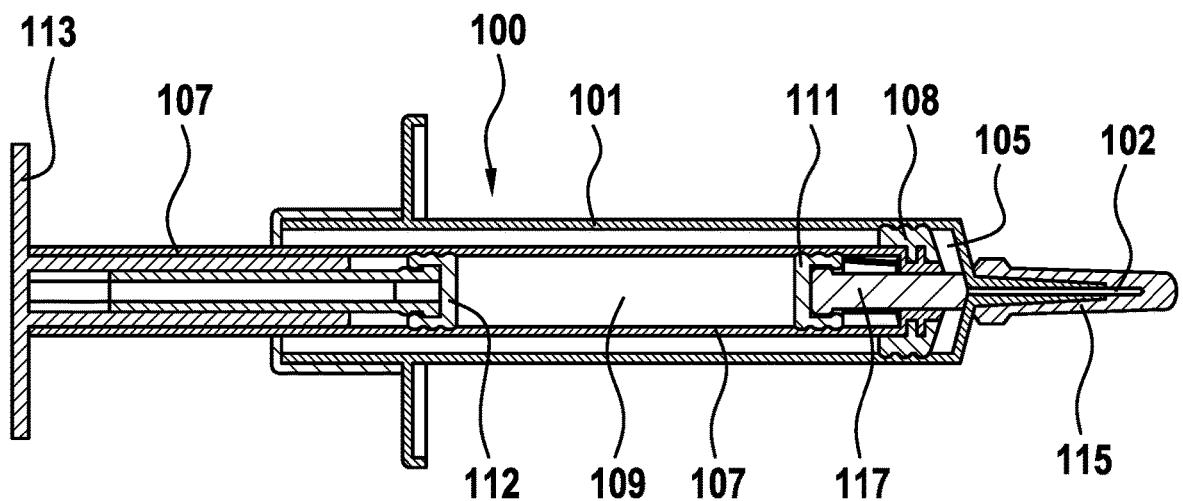
FIG. 2 shows the first embodiment of an injection device in a sectional view prior activation.
Figure 3:
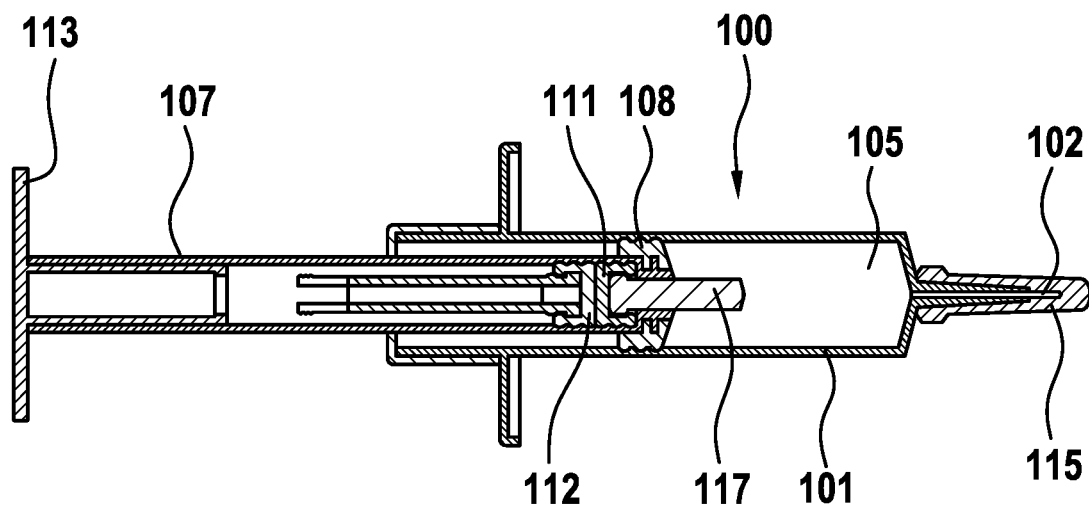
FIG. 3 shows the device of FIG. 2 after activation.
Figure 4:
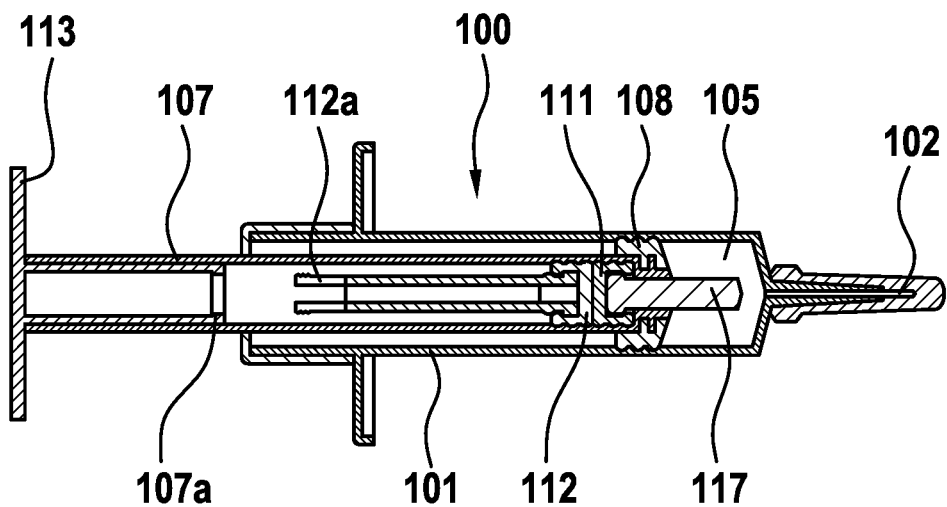
FIG. 4 shows the device of FIG. 2 during reconstitution.

The first embodiment of an injection device in form of a syringe 100 depicted in FIGS. 2 to 8 comprises a housing 101 and a needle 102 attached at its distal end. The principle of operation is demonstrated by FIG. 1. The needle 102 is in fluid communication with a first chamber 105 accommodated within the housing 101, wherein the first chamber 105 contains a first drug component, for example a lyophilized drug.

A plunger 107 is movable within the housing 101 in an axial (longitudinal) direction with regard to the syringe 100 or housing 101, wherein the plunger 107 closes the first chamber 105 at its proximal end.

Within the plunger 107 a second chamber 109 is provided containing a second drug component, for example a diluent. The second chamber 109 is closed at its distal end by a lower piston 111 and at its proximal end by an upper piston 112. The lower piston 111 and the upper piston 112 are movable within the plunger 107. The plunger 107 is formed as a sleeve-like element, wherein the hermetic seal of the first chamber at the proximal end of the first chamber 105 is provided by a distal end section 108 which has a bigger diameter than the remaining section of the plunger (except a handle 113). The diameter of the distal end section 108 corresponds to the inner diameter of the first chamber 105. The proximal end of the plunger 107 is formed as the handle 113. The distal end section of the plunger 107 comprises a, for example cylindrical through hole 114. As well as admitting the passage of fluid, this through hole 114 acts as a guide for a stud-like cotter pin 117, ensuring that piston 111 moves in a stable axial fashion.

The needle 102 is covered at its distal end by a needle boot 115. The needle boot 115 is required to prevent pressure differences from allowing air into the syringe 100.

In the initial position the lower piston 111 forming a seal between the first chamber 105 and the second chamber 109 while it is sitting in the area of an even inner surface of plunger 107. To activate mixing and/or reconstitution process of the syringe 100 shown in an initial state in FIG. 2, in a proximal stroke, a user pulls back on the plunger 107 out of the syringe 100 into a proximal direction using the handle 113 (see in FIG. 3 the fully pulled back position of plunger 107). This causes a region of low pressure to form inside the syringe 100, in particular the first chamber 105. The pressure further decreases as the plunger 107 is further pulled back. The plunger 107 is prevented from moving back to its original position shown in FIG. 2 by a ratchet system between plunger 107 and housing 101 (see FIG. 8). An outer projection from plunger 107 runs inside a track in housing 101. This projection is sprung to engage with a ratchet 101a in the track, so that plunger 107 can only move in one direction, until it has completed the full extent of its travel: then, the protrusion is guided into a smooth return track 101b. The ratchet system with ratchet 101a ensures that the plunger 107 is pulled far enough out of the syringe 100 before it begins to move back into the syringe 100 along return track 101b, thereby guaranteeing that a minimum level of suction is generated (see FIG. 3). The suction provided by the low pressure is needed to pull the first drug component through the through hole 114 within the plunger 107 and also to promote mixing of the first drug component and the second drug component within the first chamber 105.

The pressure difference between the inside of syringe, in particular inside the first chamber 105 and the second chamber 109, and atmosphere creates a force on the lower piston 111. This force is transferred through the second drug component contained in the second chamber 109 and onto the upper piston 112. They are thereby caused to move the plunger 107 down. The cotter pin 117 thereby moves through the through hole 114 and the lower piston 111 until the upper piston 112 hits the lower piston 111 (see FIG. 3). The cotter pin 117 and/or the lower piston 111 comprise a compressible outer surface which interacts with a set of longitudinal ribs 120 (web-like elements) provided at the distal end of the inner surface of the plunger 107 forming an uneven inner surface (see FIG. 7). When the lower piston 111 is pushed into the uneven area (ribs) the seal is broken. These ribs 120 force gaps to open up around the lower piston 111 and fluid can go through and therefore open a fluid communication path between the second drug component contained in the second chamber 109 and the first drug component contained in the first chamber 105 via the through hole 114. The second drug component flows out the distal end of the plunger 107 and into the first chamber 105 of the syringe 100 (see FIG. 4, it shows the position in which the second drug component has completely emptied into the first chamber 105). All of the second drug component will have passed into the first chamber 105 of the syringe 100 before the plunger 107 is pulled back completely. As plunger 107 moves back further, pressure in chamber 105 drops to near vacuum.

Once the plunger 107 has completed its stroke in the proximal direction, the ratchet mechanism will permit it to move back into the syringe 100 until pressure has equilibrated within the syringe 100 and atmosphere. This return is sudden, and the abrupt equilibration promotes mixing between the first and the second drug component in chamber 105.

Figure 6:
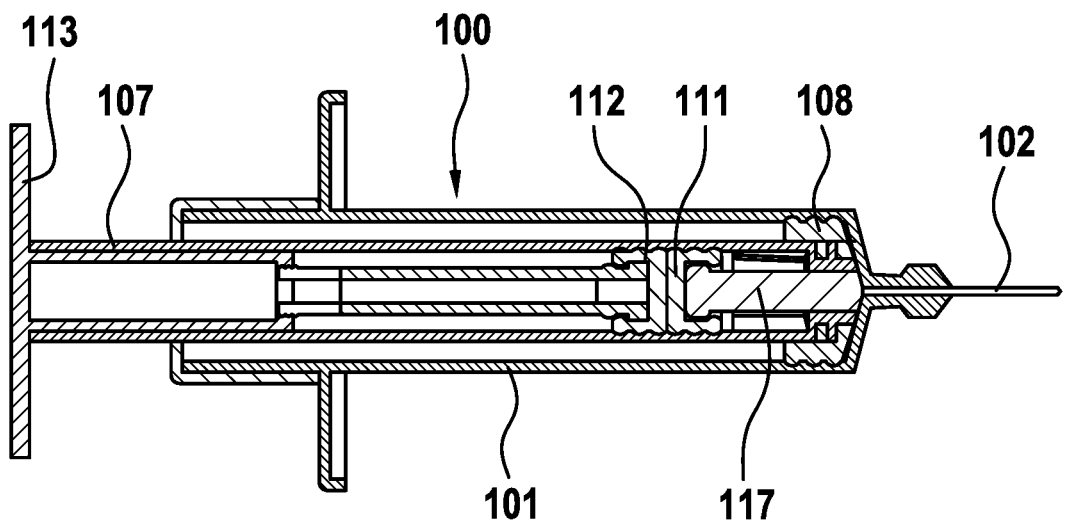
FIG. 6 shows the device of FIG. 2 after injection.
Figure 7:
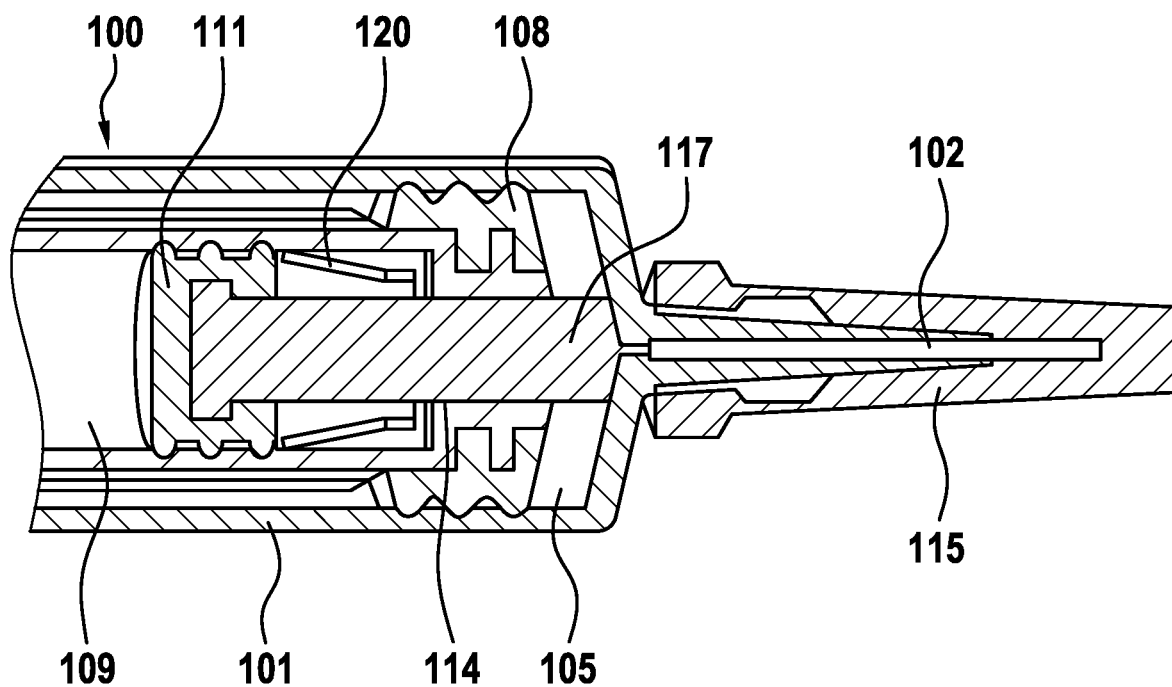
FIG. 7 shows a detail of the device of FIG. 2 in a sectional view.
Figure 8:
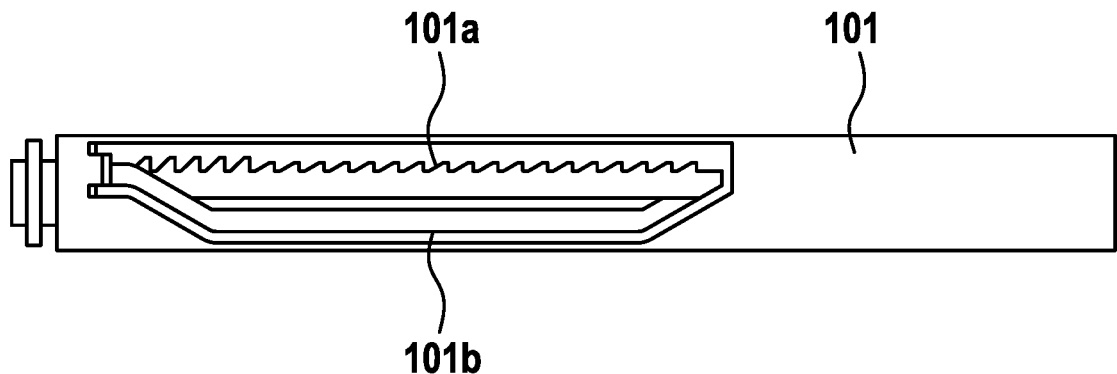
FIG. 8 shows a detail of the plunger of the device of FIG. 2.

At this point visual check of mix clarity is needed before the mixed and/or reconstituted drug comprising the first drug component and the second drug component can be injected. If it has not been fully mixed, the user must manually shake the device to fully mix the drug. Once the drug is fully mixed, it can be injected using the plunger 107 by moving it into distal direction by means of handle 113 as with any standard syringe (see FIG. 6 showing the syringe 100 post injection).

Figure 5:
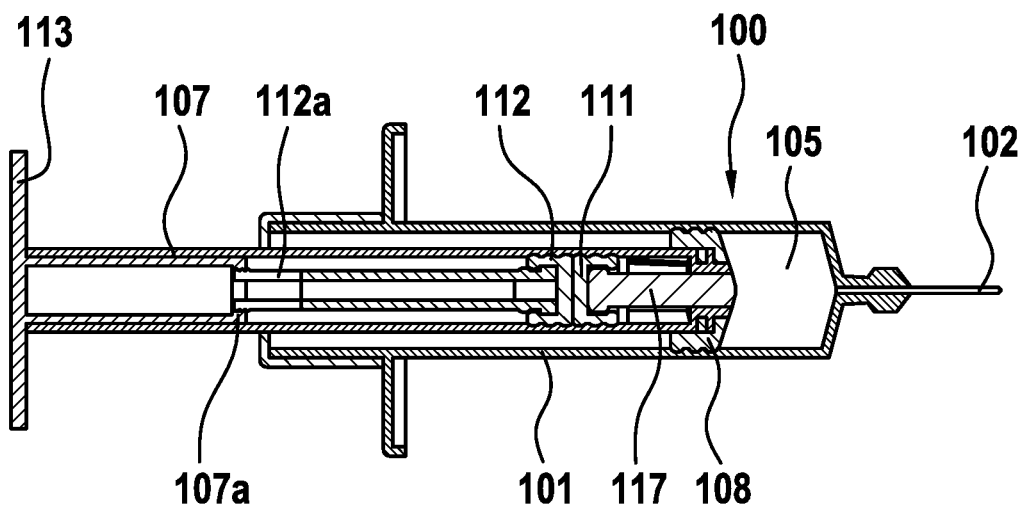
FIG. 5 shows the device of FIG. 2 at the beginning of injection.

When plunger 107 is moved to inject drug, the pressure increase within the syringe 100 causes the upper and lower pistons 111, 112 to move into proximal direction until a snap or clip member 112a at the proximal end of the upper piston 112 and snap or clip member 107a at the inner surface of the plunger 107 interact and mechanically lock (see FIG. 5, realized for example by a hook and a protrusion). This prevents any increase of pressure inside the syringe 100 from forcing the lower piston 111 and the upper piston 112 further back into the plunger 107 and therefore the second drug or the mixture of first and second drug cannot move back into the plunger 107. In this position the lower piston 111 does not interact with the ribs 120 of the plunger anymore and hence the lower piston 11 closes the second chamber 109. Note that depending on various detail design features, this may have already occurred during the sudden equilibration of pressure described above.

In an alternative embodiment, at the point where the user visually checks the clarity of the mix comprising the first and the second drug component, instead of manually shaking the syringe 100 it is allowed that the plunger 107 is continuously pulled back in order to create a region of low pressure in 105 again. This cyclical process is allowed by the ratchet mechanism forming a closed loop, which the mechanism of 107 can go around repeatably. The user may pull back the plunger and release it as many times as they like until the first and second drug components are fully mixed.

In a further embodiment the injection device is an autoinjector. This autoinjector may be constructed such that it includes an automated movement of the plunger in the reverse direction so that mixing of the first and second drug component is performed without user intervention. An optical check of clarity of the mix comprising the first and second drug component is still required from the user so that the autoinjector would need to be able to continue the mixing cycle for as long as the user deems necessary. This may be realized using the repeated creation of low pressure regions as outlined above.

The above mentioned communication between the first and the second chamber 105, 109 is provided by breaking of the seal provided by the lower piston 111 within housing 107, as the lower piston 111 interacts with the ribs 120 of the plunger 107. Alternatively, a bypass pathway may be created which allows the second drug component to flow around the piston 111. As a further alternative there may also be used some form of needle/septum interaction as depicted in FIG. 1, where a needle 122 attached to the distal end of the lower piston 111 pierces a membrane 125 of the distal end section 108 of the plunger 107.

The needle 102 may be changeable and removably attachable to the injection device.

In a further embodiment rather than the ratchet mechanism being inside the injection device 100, it could be housed outside of the injection device within a separate housing. The housing would hold syringe 100 and plunger 107, and guide their relative motion in the same way that the ratchet achieved. This will save space in the disposable device, as it removes a complex interaction between parts 100 and 107.

In a further embodiment a combined axial and rotational (twisting) motion could be conducted by the user to pull back the plunger 107, similar to those systems found in standard pen injectors, instead of the axial movement described above.

In a further embodiment it is possible to include a needle shield in the injection device. This shield would cover the needle 102 and retract as the user pushes the device against their skin for injection. Once the needle 102 is removed from the skin, the shield would move back into place and thereby activate a locking mechanism so that the user is unable to retract the needle shield again.

The above mentioned embodiments explained with reference to FIGS. 1 to 8 have the advantage that they provide an improved user operability because the user needs only to pull back the plunger until it naturally snaps back into the injection device. Further, the ratchet mechanism regulates the process so that the result is independent of user skill. Further, the user may perform a visual check of clarity of the mix of the first and second drug components. The user only needs to gently shake the injection device to ensure complete mixing of any residual first or second drug component. Additionally, during the reconstitution process air is not introduced. The injection is analogue to the standard procedure which the patient knows. Further, there is no danger of contamination during the mixing and/or reconstitution process as it all occurs within a factory-sealed environment. The mixing of the first and second drug components is very predictable and consistent. Additionally, the user has only one disposable part and does not have to ensure sterility for any part as this is maintained throughout use. Although there is use of a low pressure region to promote mixing of the first and second drug components, this low pressure does not have to be held during device storage.

Figure 9:
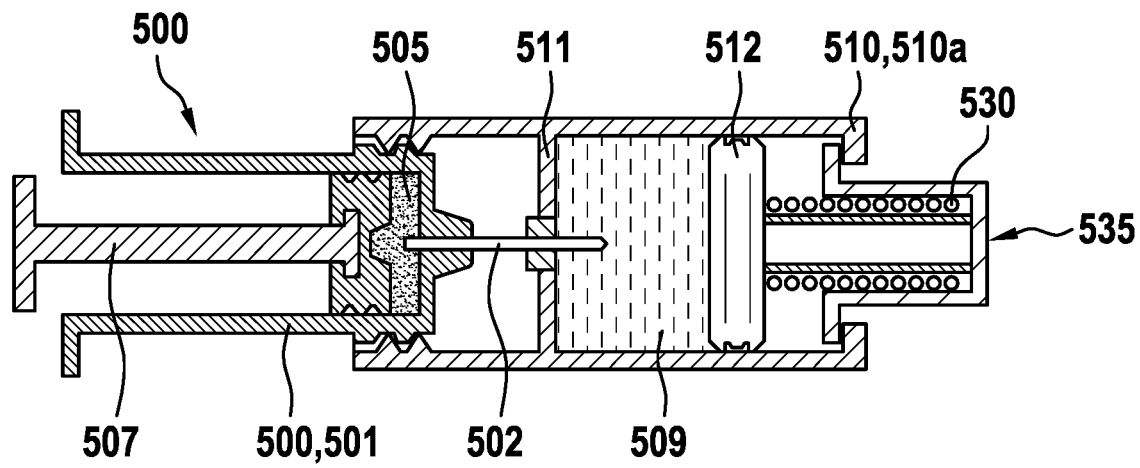
FIG. 9 shows a concept sketch of another embodiment of an injection device with a primary package in a sectional view.

The embodiment shown in FIGS. 10 to 15 and as a concept sketch in FIG. 9 comprises a syringe 500 with a housing 501 and a needle 502 attached to the distal end of the syringe 500. The needle 502 is in fluid communication with a first chamber 505 accommodated within the housing 501 of the syringe 500. The first chamber 505 is defined at its proximal end by a plunger 507. The first chamber 505 comprises a first drug component, for example a lyophilized drug. The needle 502 is suitable for injection of a drug into a patient. A minimal volume of air is held with the first drug component within the first chamber 505.

Figure 10:
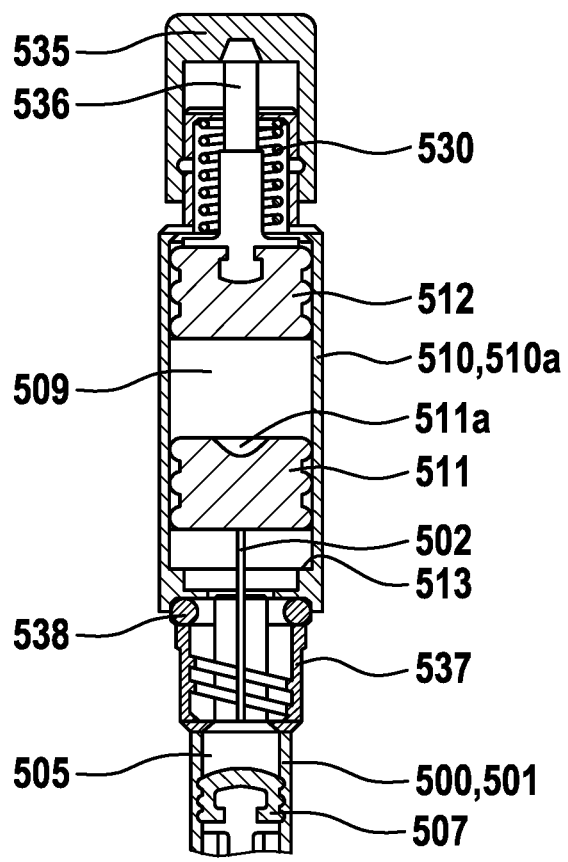
FIG. 10 shows another embodiment of an injection device with a primary package in a sectional view.

Additionally, a primary package 510 is provided comprising a housing 510a (custom housing). The primary package 510 contains within a second chamber 509 formed by its housing 510a a second drug component, for example a diluent, accommodated between a lower piston 511 and an upper piston 512. The lower piston 511 and the upper piston 512 are both moveable within the housing 510a of the primary package in an axial direction, wherein the lower piston 511 is accommodated more proximal than the upper piston 512. The lower piston 511 contains a septum seal within its body. Additionally, it comprises at its upper or distal surface a recess or indentation 511a. The upper piston 512 is in contact on its distal side with a compression spring 530 as a driving mechanism which is initially compressed and held in place by a clip mechanism 536. A cap 535 on the distal end of the primary package 510 sits over the clip mechanism 536, i.e. the cap covers the clip mechanism 536 with the spring 530. When the cap 525 is pushed downwards, e.g. into proximal direction, it will release the clip mechanism 536 and allow the spring 530 to apply an axial force into proximal direction to the upper piston 512. At the proximal end of the primary package 510 attachment means, for example one part of a luer-lock 537, is provided. As shown in FIG. 10 prior to activation of the mixing and/or reconstitution process the primary package 510 is attached to the distal end of the syringe 500 by the attachment means, for example the luer-lock 537. This luer-lock 537 provides a seal to ensure that the exposed parts of the needle 502 remain sterile until injection, e.g. the space around the needle 502 is sealed during device assembly and remains so until immediately prior to injection. Further, an O-ring 538 is provided which contacts the housing 510a of the primary package 510 and the luer-lock 537 forming an additional seal.

A different attachment means between the syringe 500 and the primary package 510 can be used, rather than luer-lock. Any attachment mechanism must remain secure over a shelf-life of one year and additionally be easy to engage and disengage by hand.

In an initial position shown in FIG. 10 after attachment of the primary package 510 to the distal end of the syringe 500 by the luer-lock 537 the needle pierces the lower piston 511 to a certain extend but does not penetrate the septum seal within the body of the lower piston 511.

Figure 11:
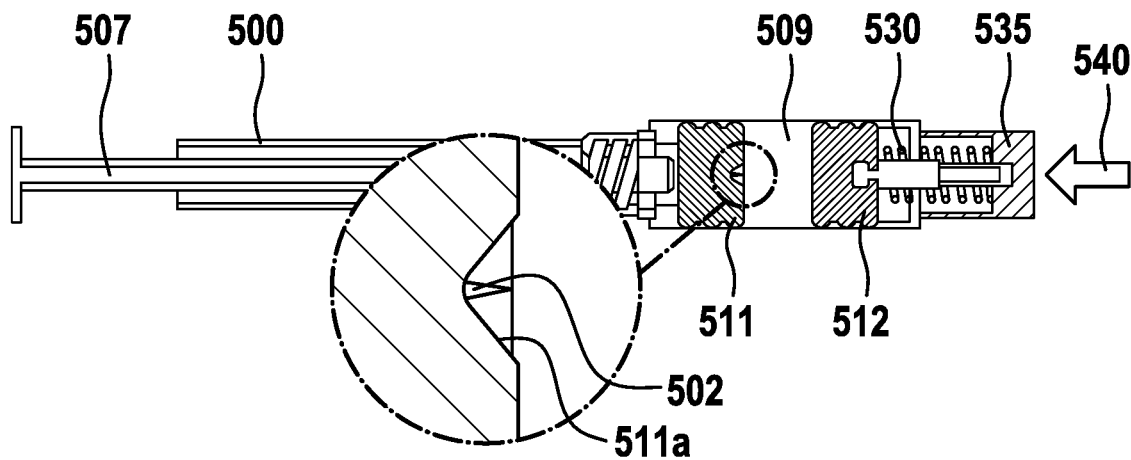
FIG. 11 shows the embodiment of FIG. 10 during a first step of a mixing/reconstitution process in a sectional view.
Figure 12:
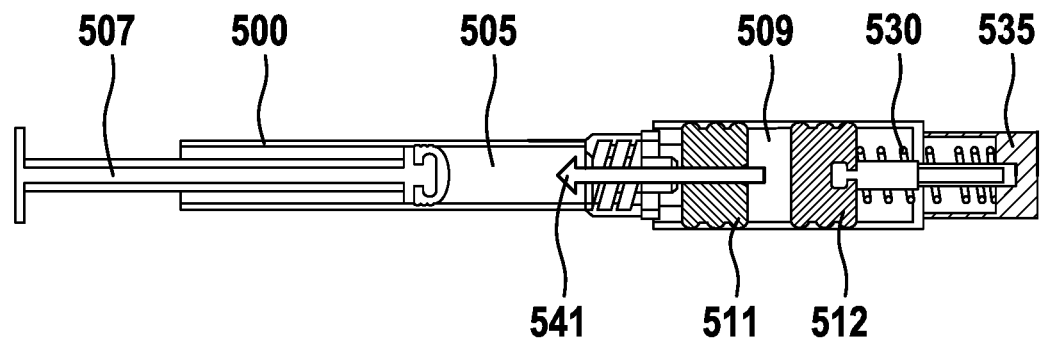
FIG. 12 shows the embodiment of FIG. 10 during a second step of a mixing/reconstitution process in a sectional view.

In order to start with the mixing and/or reconstitution process the user presses on the cap 535 and moves it into proximal direction (see arrow 540 in FIG. 11). Thereby, the clip mechanism 536 retaining the compression spring 530 is disengaged and allows the compression spring 530 to extend (see FIGS. 11 and 12). The disengagement may work in one embodiment as follows. The upper piston 512 may comprise one flexible clip or more than one flexible clips (not shown) which pass through a hole in the housing 510a, and act against an upper face of housing 510a. The cap 535 comprises a recess (not shown) at its front end over the respective flexible clip. As cap 535 is pressed down, the clip enters the respective recess. Each recess is chamfered so that as the clips enter, they are compressed together, disengaging them from housing 510a allowing the spring 530 to extend in axial direction. Both, the force from the extending spring 530 and from the user's hand can contribute to push the subsystem comprising the second drug component (the second drug component plus the upper and the lower piston 511, 512) along an axial proximal direction of the primary package 510. Thereby the needle 502 is forced to penetrate the septum seal of the lower piston 511 thereby forming a fluid communication between the second chamber 509 and the first chamber 505 of the syringe 500. The lower piston 511 is stopped from moving further by an end-stop feature within the primary package 510, for example a projection 513 at the inner surface of the housing 510a (see FIG. 10). In this position the distal end of the needle 502 is located within the recess 511a of the lower piston 511. The upper piston 512 is further forced to move into proximal direction and into the direction of the lower piston 511 thereby increasing the pressure within the second chamber 509 and pushing the second drug component through the needle 502 into the first chamber 505 (see arrow 541 in FIG. 12).

Figure 13:
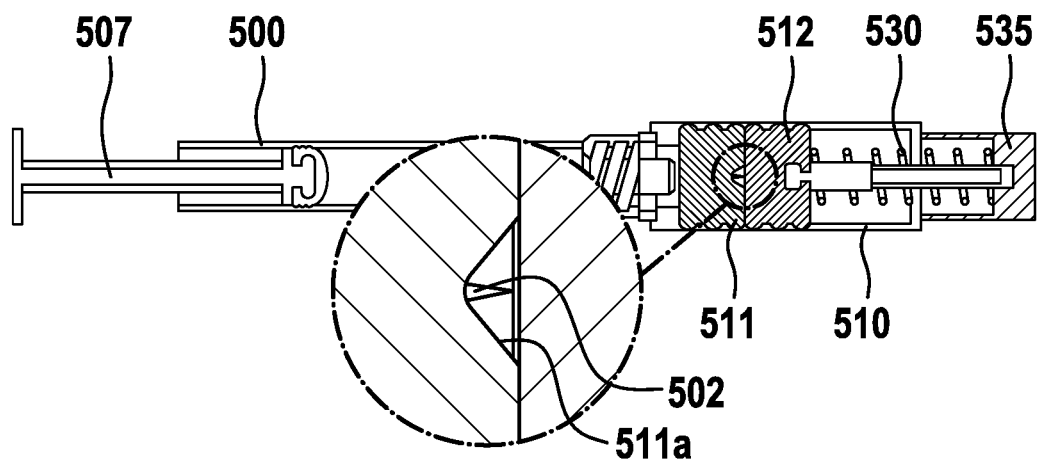
FIG. 13 shows the embodiment of FIG. 10 during a third step of a mixing/reconstitution process in a sectional view.
Figure 14:
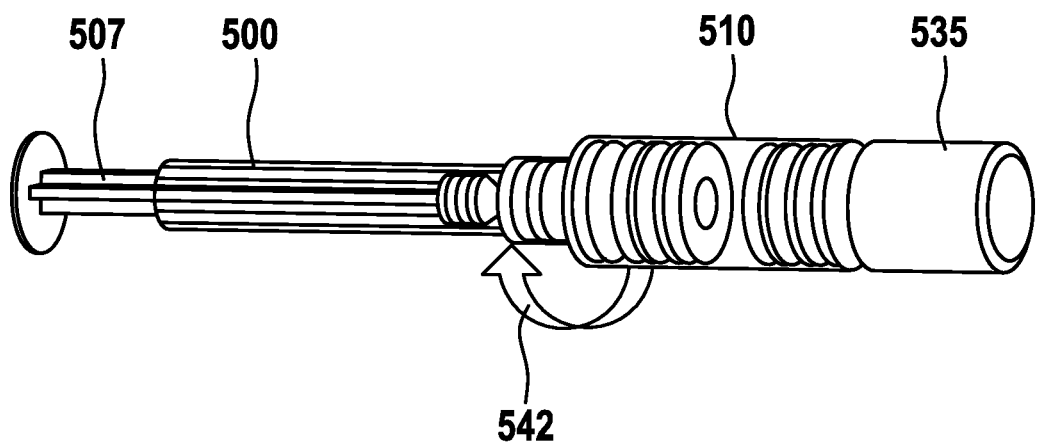
FIG. 14 shows the embodiment of FIG. 10 during a forth step of a mixing/reconstitution process in a sectional view.
Figure 15:
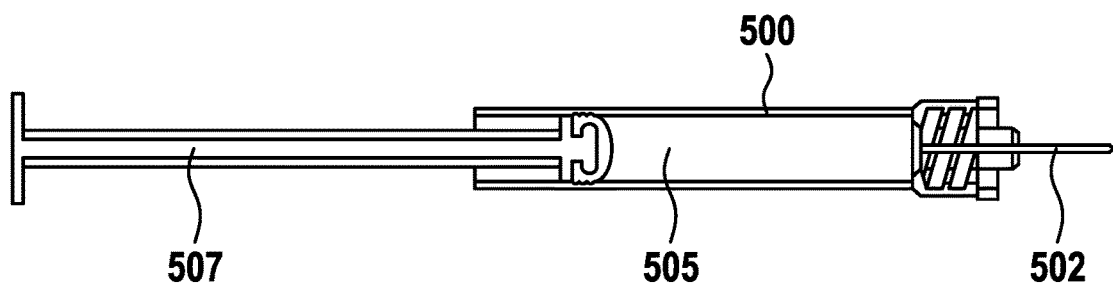
FIG. 15 shows the syringe of the embodiment of FIG. 10 prior injection in a sectional view.
Figure 16:
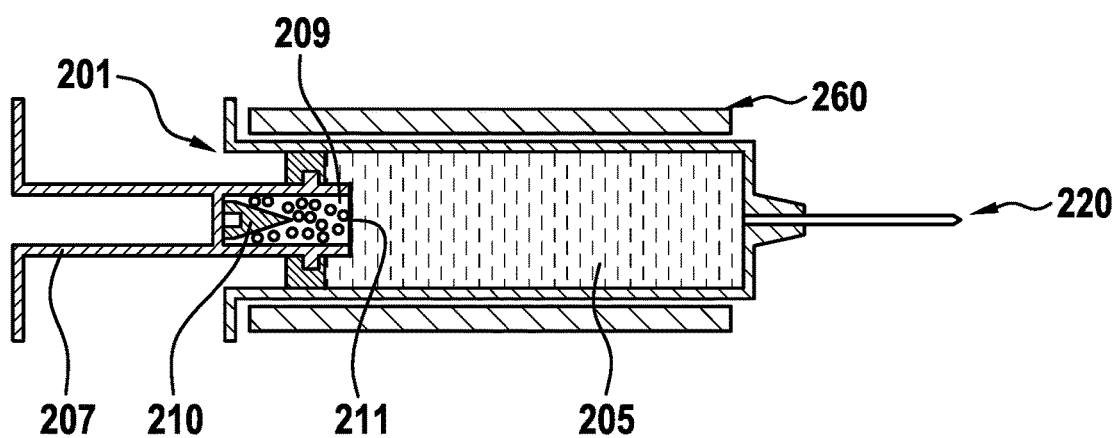
FIG. 16 shows an injection device and a detail of a mixing unit of an embodiment of an inventive system in a sectional view as a concept sketch.

The recess 511a at the lower piston 511 allows the needle 502 to protrude through the lower piston without ever touching the upper piston 512 (see FIGS. 11 and 13). It is noted that the lower piston 511 and the upper piston 512 eventually met when whole content of the second drug component is transferred from the second chamber 509 into the first chamber 505. The recess 511a has the advantage that if the upper piston 512 contacts the lower piston 511 the needle 502 would not contact the upper piston 512 and consequently the flow of the second drug component through the needle 502 would not stop. In another embodiment the recess may be located in upper piston 512 rather than in lower piston 511, for the same effect.

When the second drug component enters the first chamber 505 it will be under substantial pressure which creates a high speed jet (for example with a fluid velocity of 2.5 m/s and faster, preferably with a velocity of 5 m/s and faster) in the case that the second drug component is fluid. This jet dislodges the first drug component and causes turbulent mixing. All of the second drug component will be mixed into the first drug component by the time the upper piston 512 finishes expelling of the second drug component into the first chamber 505. The spring 530 generates all of this pressure to drive the second drug component and ensures reliable and repeatable mixing independent of user strength or skill. The user may visually check that the first and second drug components are fully mixed.

Then the user may unscrew (see arrow 542 in FIG. 14) or otherwise detach the primary package 510 from the syringe 500. The syringe is now ready to inject (see FIG. 15) the mixed and/or reconstituted drug contained within the first chamber 505.

In another embodiment rather than using a standard syringe 500 for the accommodation of the first drug component, a cartridge could be used to be placed in another device for injection.

In one embodiment the plunger 507 within the syringe 500 may be custom shaped to improve the mixing resulting from the fluid jet. For example, the plunger 507 may comprise one or more concave cavities at its front end defining the first chamber 505. Within such cavity the jet of fluid is deflected out to better penetrate the corners of first chamber 505. Alternatively or additionally, one or more vanes at the front end of plunger 507 defining the first chamber 505 may achieve a similar effect.

In another embodiment the proximal end of the needle 502 within the syringe 500 may be shaped so that a jet of fluid is directed towards the proximal direction, keeping the majority of turbulent mixing close to the first drug component. For example, the proximal end of needle 502 may have a bend so that the jet enters first chamber 505 at an oblique angle, setting up swirl flows to promote mixing. Alternatively or additionally, through holes within the side wall of the proximal end of the needle 502 may be provided in order to create multiple jets.

In a further embodiment the primary package 510 may be housed inside an autoinjector so that manual injection is not necessary. The autoinjector would have to allow removal or separation of the primary package 510 prior to insertion.

In another embodiment the attachment of the syringe 500 and the primary package 510 may be more permanent. For example the syringe 500 and the primary package 510 may be welded together, with the weld creating a hermetic seal that replaces the function of the seal 538 and the luer-lock connector 537. In this case, a mechanism must allow the syringe 500 and the primary package 510 to separate before injection. This may be realized by a snap mechanism, wherein the housing 501 of the syringe 500 and the housing 510a of the primary package 510 may simply snap apart under user pressure.

In a further embodiment, the primary package 510 may comprise two separate parts, one holds the spring and the other one holds just the second chamber with the second drug component and the upper and lower piston 511, 512. This would remove the need to weld the primary package 510 together during manufacture. The parts would have to interlock prior attachment to the syringe 500.

In further alternative embodiments, the force for driving the upper piston 512 may be generated not by a compressed spring 530 as explained above but instead by another driving mechanism, for example by a gas spring or by a linear electromechanical actuator.

In another embodiment the sizes of the first chamber 505 and the second chamber 509 as well as the needle gauge can be customized in order to create a suitable jet profile for effective mixing of the particular first and second drug components.

The needle 502 could, instead of being staked into the syringe 500, be changeable. In this case one needle may be used for mixing and/or reconstitution but the user swaps it for a separate, sterile needle for injection.

In a further embodiment the mixing and/or reconstitution process may be activated by movement of the primary package, for example its housing, rather than a pushing onto the cap 535. For example, when the user attaches the primary package 510 to the syringe 500 the lower and upper pistons 511 are automatically driven such that the needle 502 fully penetrates the septum, starting the flow of the second drug component into the first chamber 505.

The advantage of the embodiment explained above with regard to FIGS. 9 to 15 consists therein that the user convenience is extremely good because the user has only to press a button on the distal end of the device and wait until mixing and/or reconstitution is complete. This may be visually checked by the user. Then, the user may unscrew the syringe 500 from the primary package 510, expels air by priming as usual and injects the drug. There is no danger of contamination during the mixing and/or reconstitution process as it all occurs within a factory-sealed environment. The mixing is very predictable and consistent and the user has only two disposable parts, namely the primary package 510 and the syringe 500. The user does not have to ensure sterility for any part as this is maintained throughout use.

The embodiment described in FIGS. 17 to 28 comprises an injection device in form of a syringe 200 and a mixing unit in form of a base station 250. The syringe 200 comprises a housing 201 with a first chamber 205 and a plunger 207 which closes the first chamber 205 at its proximal end. At its distal end the plunger 207 forms a second chamber 209 within a respective inner space of the plunger 207. The first chamber 205 contains a first drug component, for example a diluent, wherein the second chamber 209 contains a second drug component, for example a lyophilized drug. Additionally, a moveable slug-like element 210 with a magnetic or paramagnetic characteristic is provided within the second chamber 209. The distal end of the second chamber 209 of the plunger 207 is covered by a seal 211. The seal may be realized by a foil or membrane, for example comprising or consisting of an aluminium-polymer laminate or a low-permeability polymer such as a cyclic olefin. At the distal end of the housing 201 of the syringe 200 a needle 202 with a needle cover 215 is attached. The needle 202 is in fluid communication with the first chamber 205 of the syringe 200. The needle cover 215 protects the needle 202, avoids its contamination and prevents the user from needle sticks.

Figure 24:
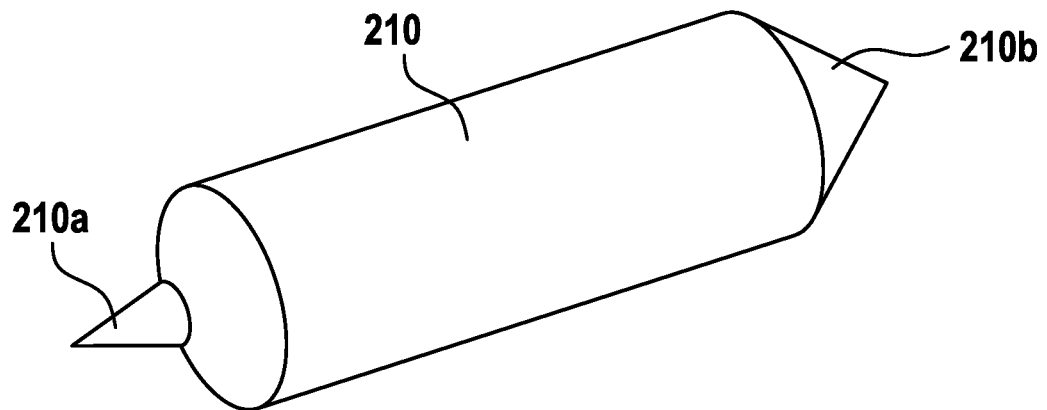
FIG. 24 shows a slug-like element of the system of FIG. 17 in a perspective view.
Figure 25:
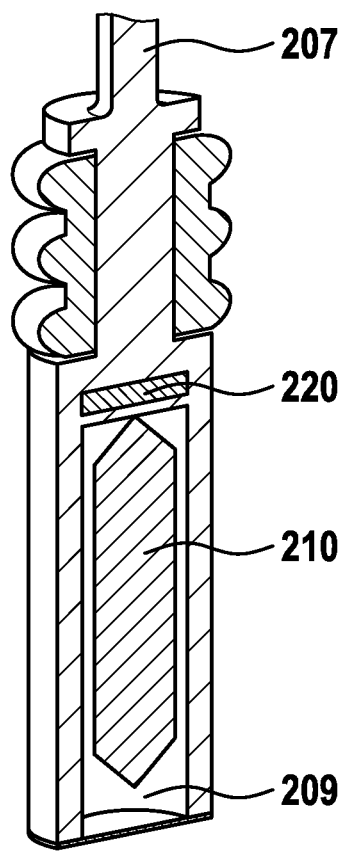
FIG. 25 shows a distal section of a plunger of another embodiment of an injection device in a perspective and sectional view.

The slug-like element 210 may comprise or is composed of, for example, at least one of the following materials comprising sintered Neodymium-Iron-Boron (NdFeB), preferably with a medical-grade coating, Samarium-Cobalt (SmCo) and Aluminium-Nickel-Cobalt (AlNiCo). The middle or main section of the element 210 is preferably formed as a cylinder. Alternatively, it may have a shape of a barrel or of a section of a sphere. One distal end 210a of this element 210, which is shown in FIG. 24 in detail, may be shaped as a sharp tip to puncture the seal 211.

Additionally, the proximal end 210b of the element 210 may be tapered in order to help the element 210 to slide back up into the plunger 207, so that it does not get trapped between the plunger 207 and the inner wall of the syringe housing 201, thereby preventing full injection of the mixed and/or reconstituted drug.

The seal 211 may be provided such that it bursts in a way that does not create loose parts. Equally, the proximal end of the needle 202 may be made too small for foil parts to enter, or a filter may be added inside the syringe (e.g. at the distal end of the first chamber, within the first chamber 205) preventing that foil parts enter the needle 202.

The base station 250 comprises a series of electromagnetic coils 260a plus milled steel pole pieces 260b accommodated in between two adjacent electromagnetic coils 260a to guide the magnetic flux and improve efficiency. The electromagnetic coils 260a and steel pole pieces 260b together form the electromagnetic unit 260. The electromagnetic unit 260 encases a cylindrical opening 265 which is provided to receive the distal end of the syringe 200. An inserted syringe 200 within the opening 265 is shown for example in FIGS. 17, 19, 20, and 21. The base station 250 further comprises a control unit 270 and a power supply with batteries 273 in order to provide electrical energy for the components of the base station 250. Further, a button 275 is provided by pressing of which the mixing and/or reconstitution of the first and second drug component may be activated by the user when the syringe 200 is inserted in the opening 265. The opening of the base station 250 may contain a sensor for the syringe 200 recognizing the correct and full insertion of the syringe 200 within the opening 265. In case the sensor does not notice a syringe 200 correctly inserted within the opening 265 an activation of the button 275 shall not start the mixing and/or reconstitution step.

In the first step, the syringe 200 is inserted into the opening 265 of the base station 250 (see FIG. 18) so far that its body 201 is fully received by the opening 265 (see arrow 213). By pushing the button 275 the user activates the electromagnetic unit 260 energizing the coils 260a so that a large force into an axial direction of the syringe 200, for example a distal direction, is exerted on the slug-like element 210 during a pre-determined time period, causing it to puncture the seal 211. Thereby it is allowed to the first and second drug component to mix within the first chamber 205, for example to reconstitute both components.

In one embodiment the base station 250 comprises a separate interlock system holding the syringe 200 within the opening 265 of the base station 250 until mixing is complete.

Figure 20:
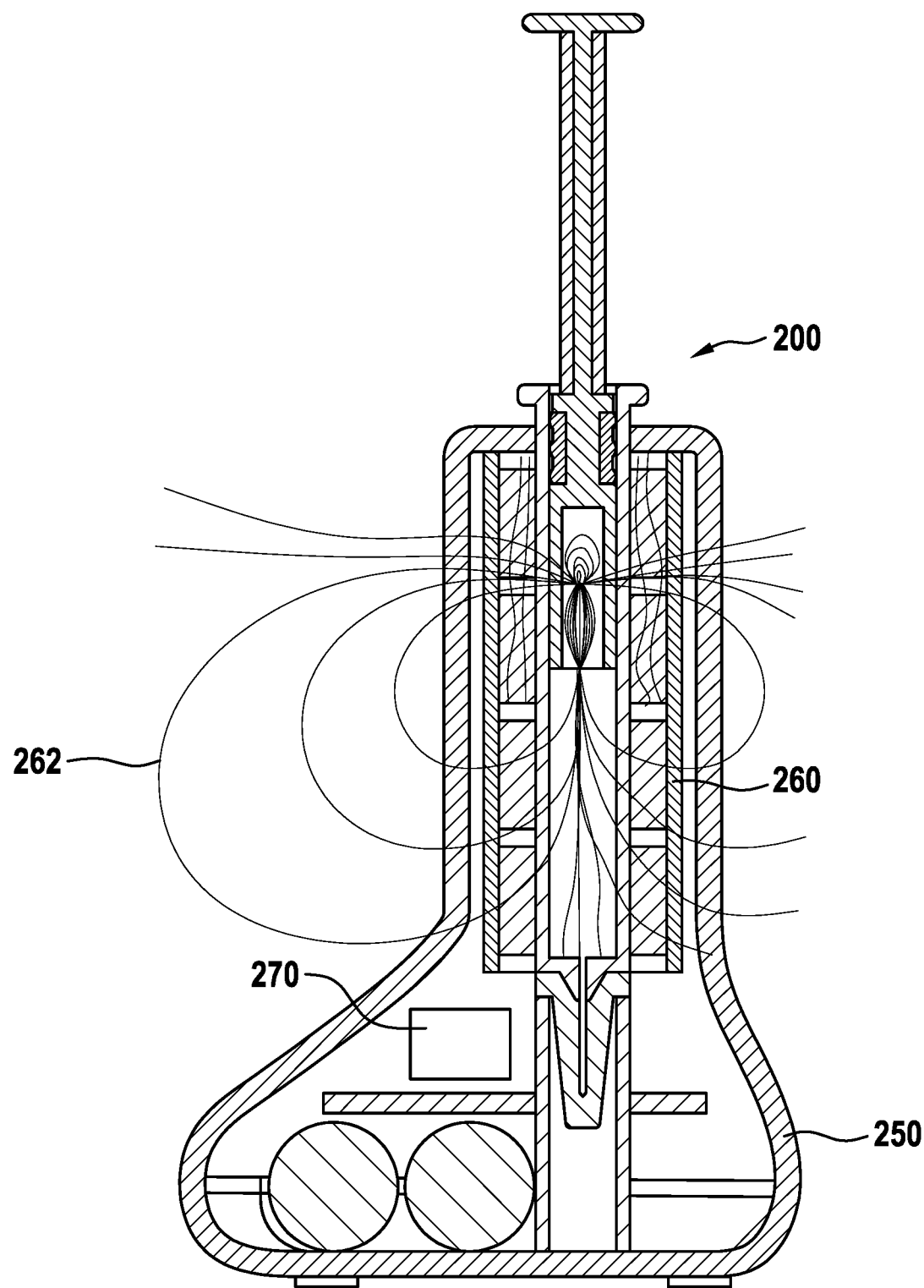
FIG. 20 shows the system of FIG. 17 after activation of the mixing and/or reconstitution step and the initial electromagnetic field produced by the electromagnetic unit in a sectional view.
Figure 21:
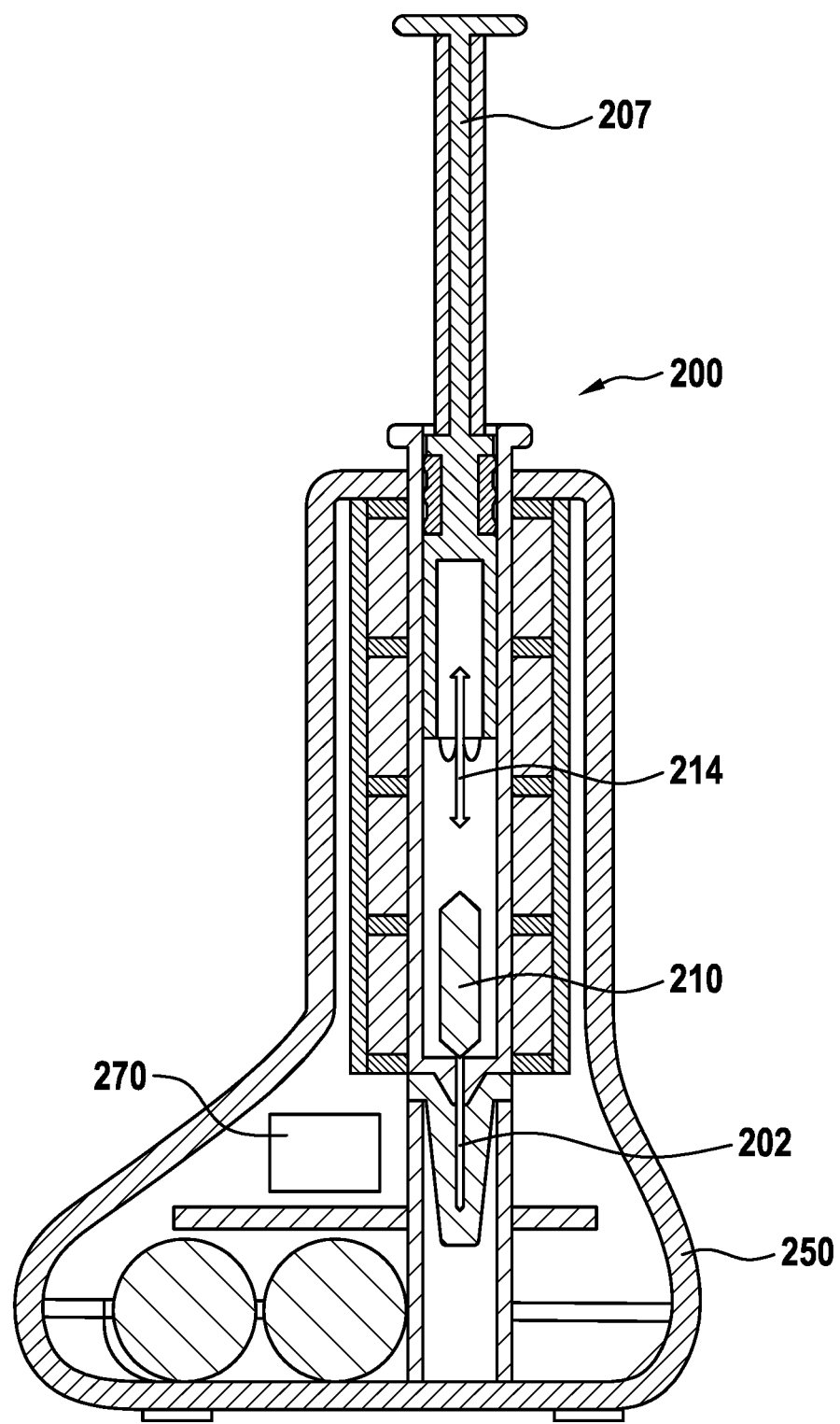
FIG. 21 shows the system of FIG. 17 during the mixing and/or reconstitution in a sectional view.

Once the element 210 has punctured the seal 211 it is free to move along the entire length of the first chamber 205 into an axial direction of the syringe 200 back and forth (see arrow 214). FIG. 20 shows lines of magnetic flux with flux density, for the initial stage, in which the slug-like element 210 is accelerated in order to pierce the seal 211. The lines of the magnetic field are marked with the reference number 262. Afterwards, the coils 260a and the magnetic element 210 form a brushless linear motor, i.e. a Lorentz force device, whereby energizing different coils in different directions and at different times causes the element 210 to move backwards and forwards in the axial (longitudinal) direction (arrow 214) of the syringe 200 within a pre-determined time period to effect mixing within the first chamber 205 (see FIG. 21). In one embodiment the base station 250 comprises four coils 260a accommodated side by side along the axial direction (see arrow 214), wherein at any one time, two coils 260a are active (see FIG. 20) alternating with the other two coils 260a. The two active coils 260a are energized in opposite directions, and interact with the two magnetic poles of the element 210 to generate an axial force such that, in one step, one coil 260a repels one magnetic pole of the element 210 and the other coil 260 of the two active coils attracts the other magnetic pole of the element 210. Only energizing coils 260a close to element 210 improves the efficiency of the system. By setting precise levels of power in each coil 260a, the speed and position of the element may be accurately controlled. If each coil 260a has a resistance of 40 Ohms, the drive system may include a boost power supply, e.g. providing 200 V, driving the coils 260a via a half bridge for 0.1 seconds. This could generate 1 kW in the coils, which would generate the large forces needed to initially puncture the foil seal. The control unit 270 of the base station 200 provides a predefined number of cycles of energizing different coils of the electromagnetic unit 260 that guarantees a homogenous reconstituted or mixed drug. At the end of the process (see FIG. 22), the element 210 rests in a position within the previous second chamber 209 of the plunger 207 whereby it does not hinder injection. As shown in FIG. 24, the element 210 has a tapered proximal end 210b to help it re-enter the plunger 207. By means of the control unit 270 which is connected with the electromagnetic unit 260 a smooth slide of the element 210 into the plunger 207 is provided during injection.

Figure 22:
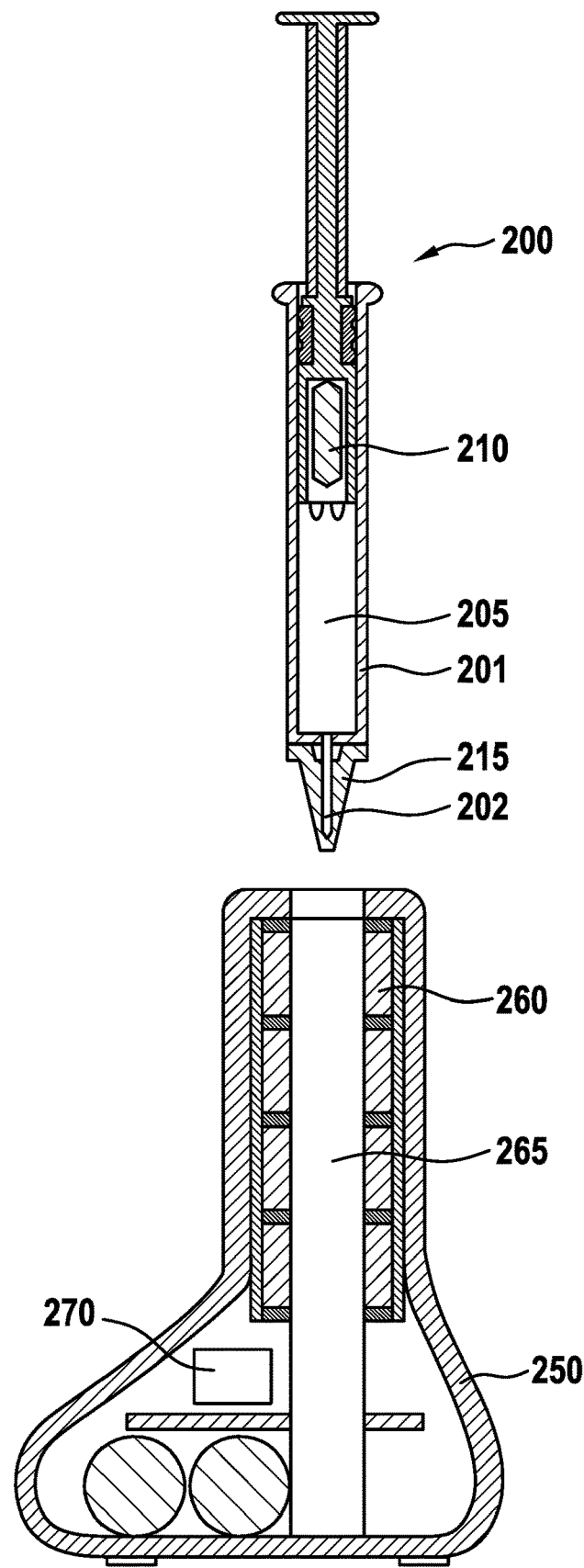
FIG. 22 shows the system of FIG. 17 after the mixing and/or reconstitution step and during withdrawal of the injection device from the mixing unit in a sectional view.
Figure 23:
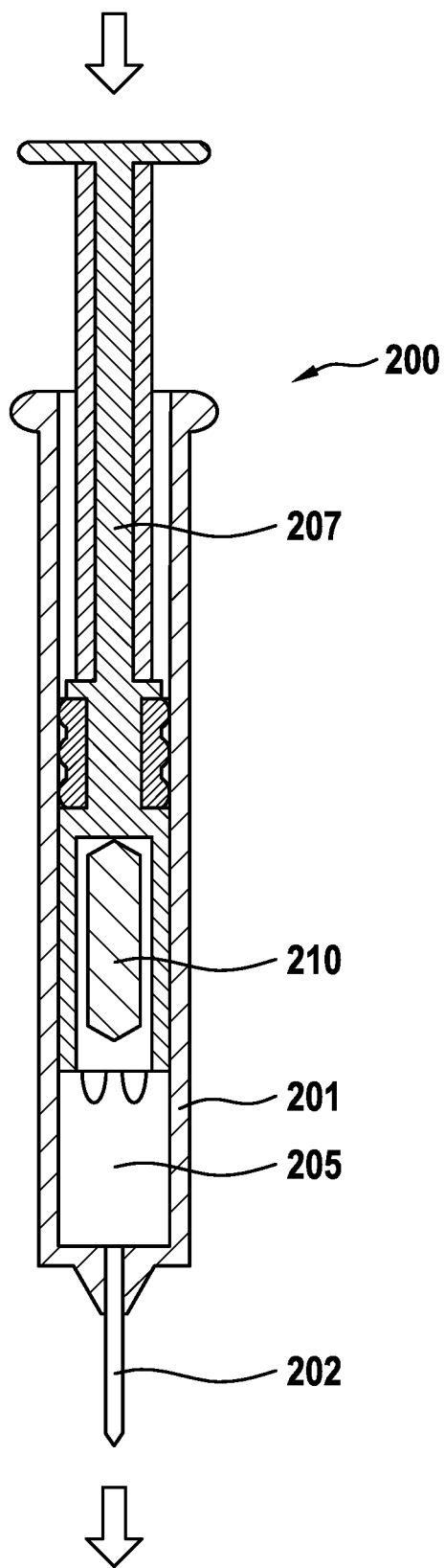
FIG. 23 shows the injection device of the system of FIG. 17 during drug administration.

Finally, as shown in FIG. 22, the syringe 200 is removed from the base station 250. In order to inject the mixed and/or reconstituted drug containing the first and the second drug component the user removes the needle cover 215, expels any air from the syringe by means of priming and finally injects the drug mixture (see FIG. 23).

Figure 17:
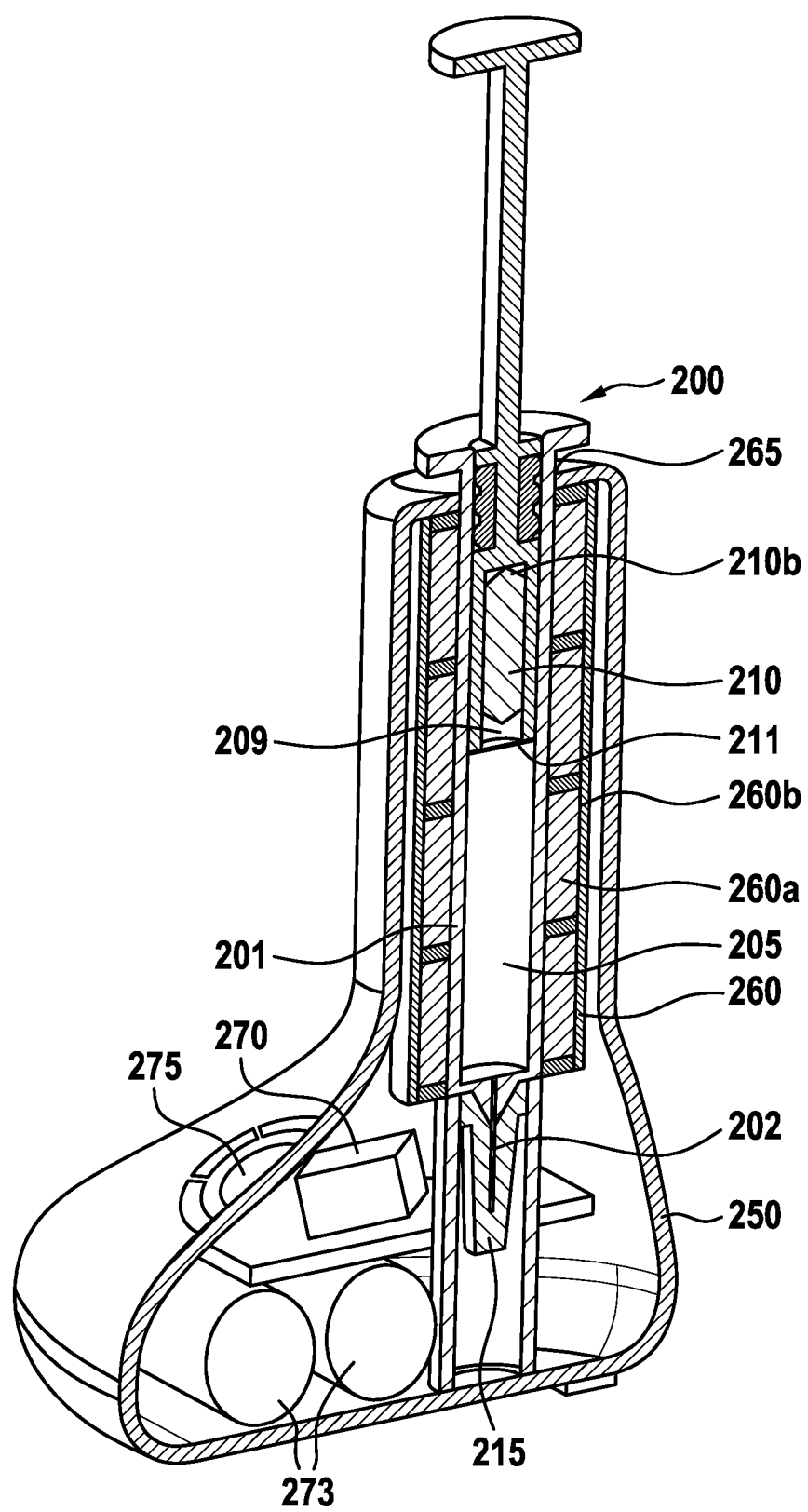
FIG. 17 shows an injection device received by a mixing unit of another embodiment of an inventive system in a perspective and sectional view prior activation of the mixing and/or reconstitution step.
Figure 18:
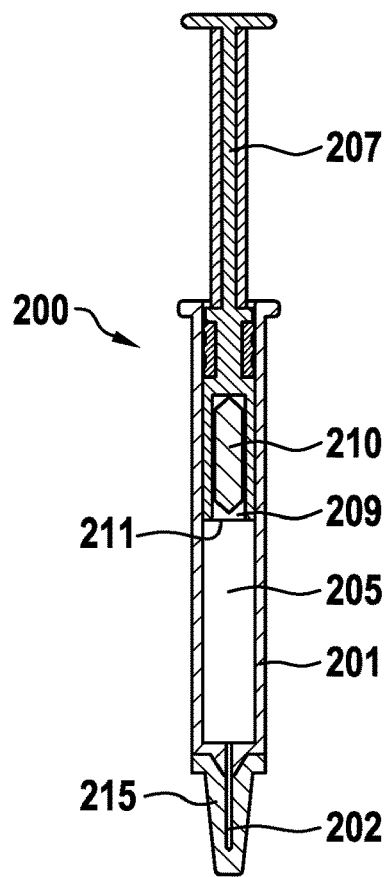
FIG. 18 shows the system of FIG. 17 prior to insertion of the injection device into the mixing unit in a sectional view.
Figure 18:
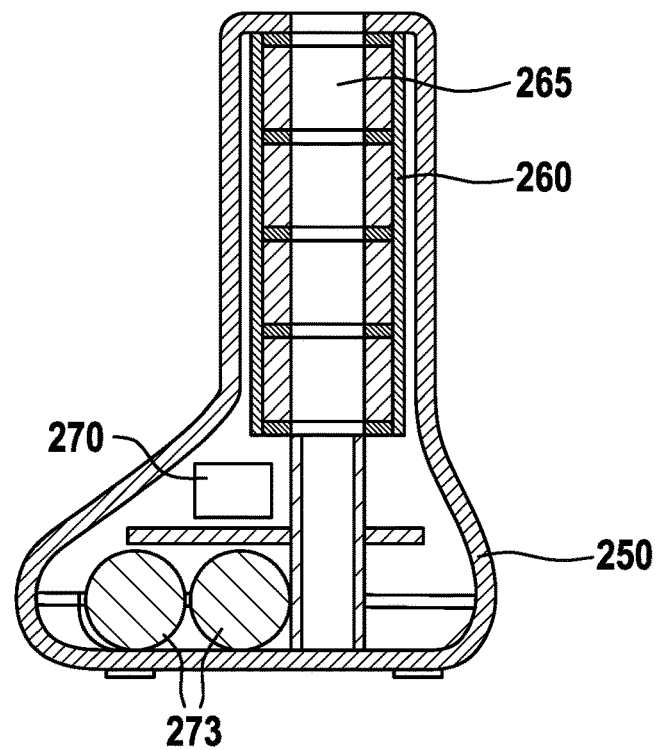
Figure 19:
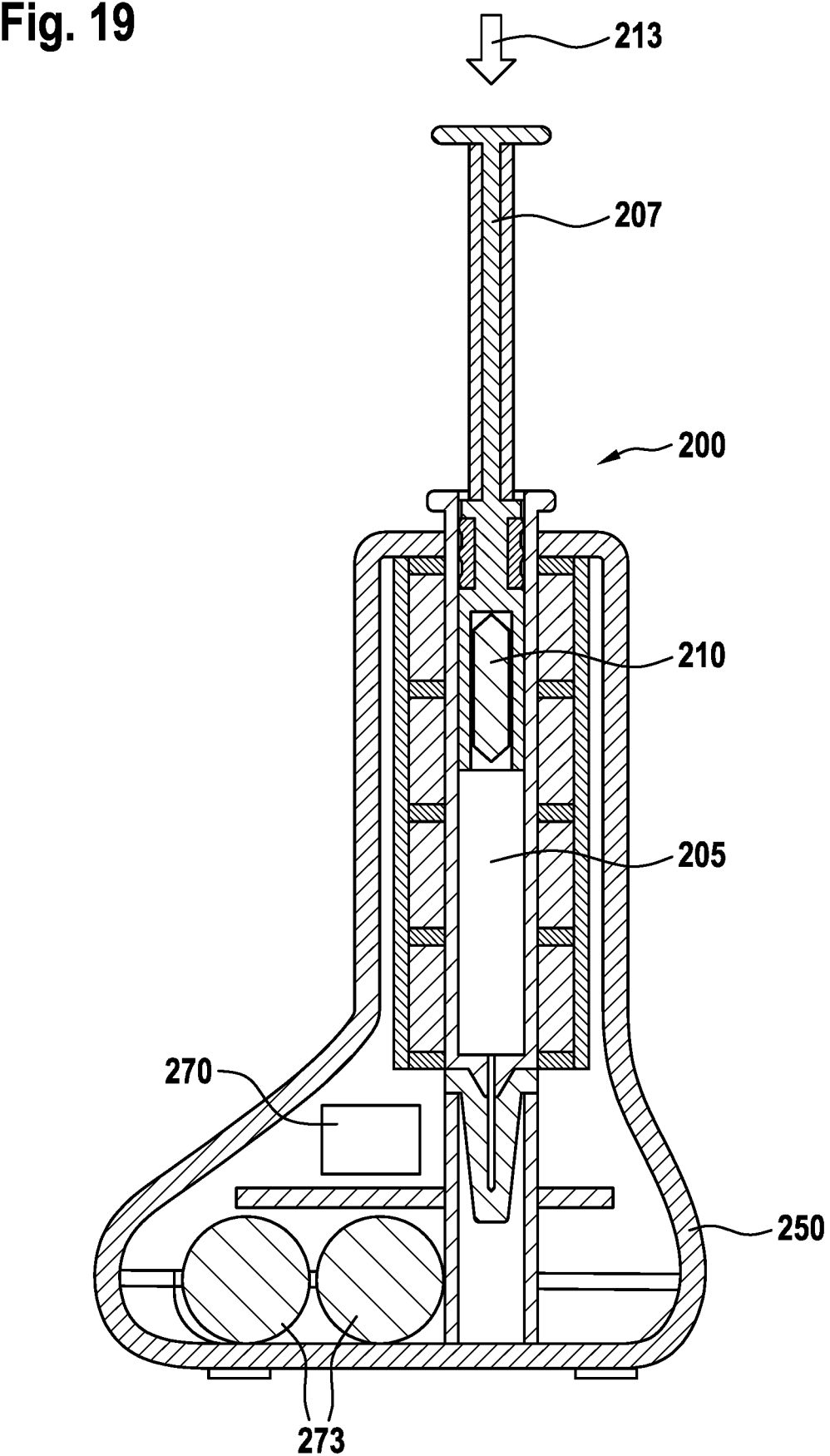
FIG. 19 shows the system of FIG. 17 after insertion of the injection device into the mixing unit in a sectional view.
Figure 26:
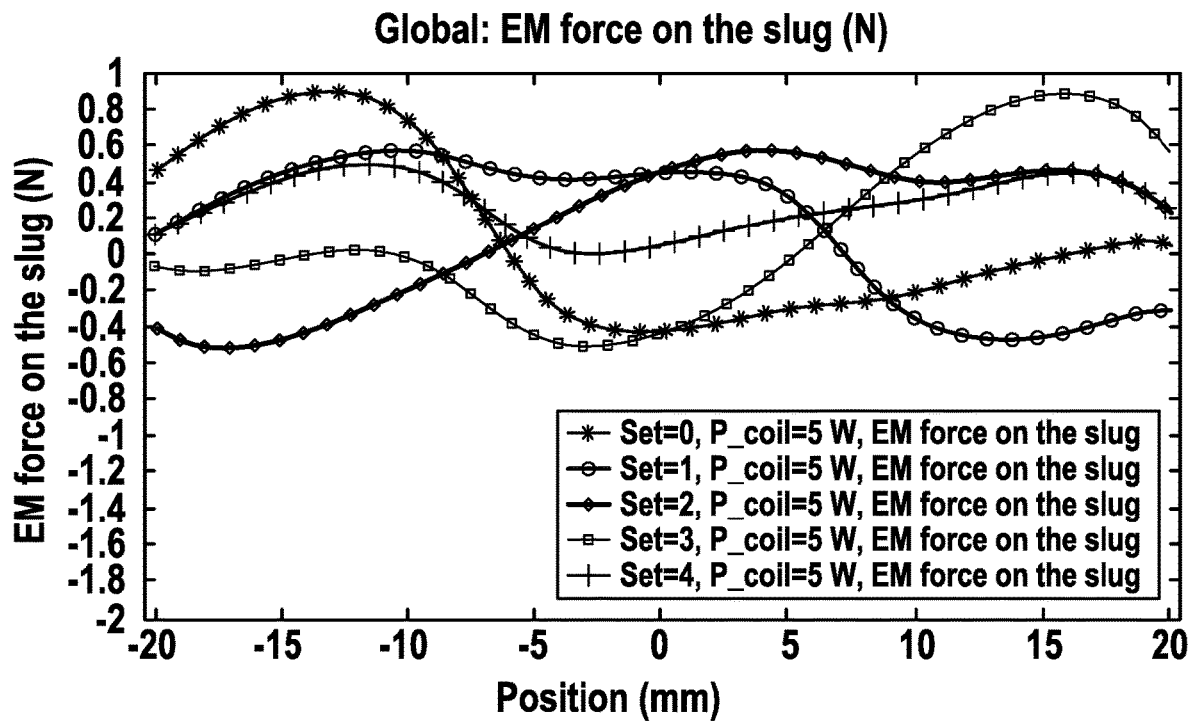
FIG. 26 shows a first set of force profiles for different active coil sets of the electromagnetic unit of the mixing unit of FIG. 17 in a diagram in which the electromagnetic force on the slug-like element is shown as a function of the axial position within the opening.
Figure 27:
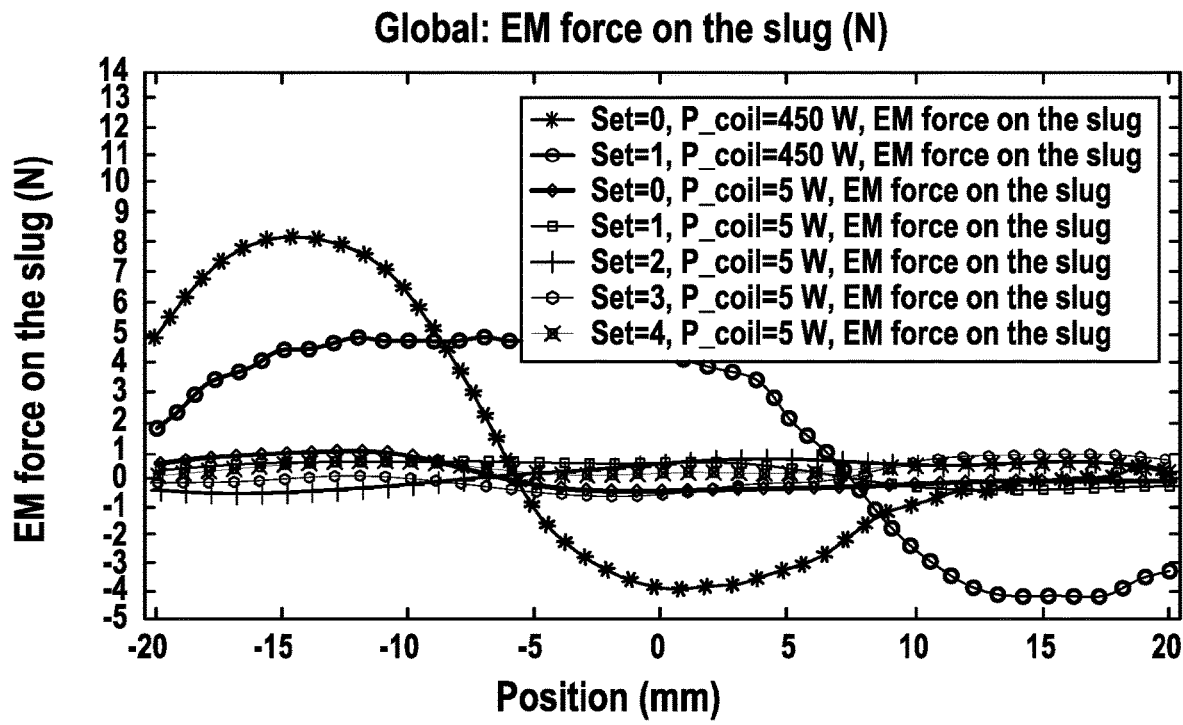
FIG. 27 shows a second set of force profiles for different active coil sets of the electromagnetic unit of the mixing unit of FIG. 17 in a diagram in which the electromagnetic force on the slug-like element is shown as a function of the axial position within the opening.

The FIGS. 26 and 27 show the forces generated at 10W and 900W for five different coils of the electromagnetic unit 260, respectively, for the geometry shown in FIG. 17. At 10W, forces are ample to dislodge the second drug component and mix the first and second drug component reliably. At 900W, forces are adequate that the element 210 is accelerated and punctures the seal 211, subject to the geometry of the slug-like element 210. This high power is only needed for a very brief period of time, namely the time in which the seal 211 is punctured, so total energy used is low and the coils of the electromagnetic unit 260 do not overheat.

In another embodiment an additional plate-like metal element 220, made from a soft magnetic material for example comprising steel, could be used to hold the paramagnetic or magnetic element 210 in place until the syringe 200 is placed in the base station 250 and activated, and also to keep the element 210 inside the plunger during injection. The plate-like element 220 is accommodated within the plunger 207 close to the proximal end of the second chamber 209 (see FIG. 25). The plate-like element 220 is as close as possible to element 210, by making the wall between it and chamber 209 as thin as practical, preferably the thickness may be less than 1 mm. This means that element 220 can be small and still provide sufficient attraction to element 210. For example, element 220 may have a thickness of more than 0.5 mm, preferably more than 1 mm. The plate-like element 220 prevents that no amount of inadvertent agitation during (e.g.) shipping or dropping the device prior to use will cause the seal 211 to rupture. In an alternative embodiment the element 220 could be a separate element which the user has to remove or an element that is dislodged on insertion of the syringe 200 in the base station 250. For example, the element may be a steel collar piece accommodated around the outside of housing 201 of the syringe 200, which is slid away on insertion into base station 250. Anyhow, the element 220 generates a small enough force that the coils of the electromagnetic unit 260 can easily overcome it.

If the slug-like element 210 is a permanent magnet, it is preferred to use a medical-grade coating to prevent contact between the magnetic material and the first or second drug component.

Figure 28:
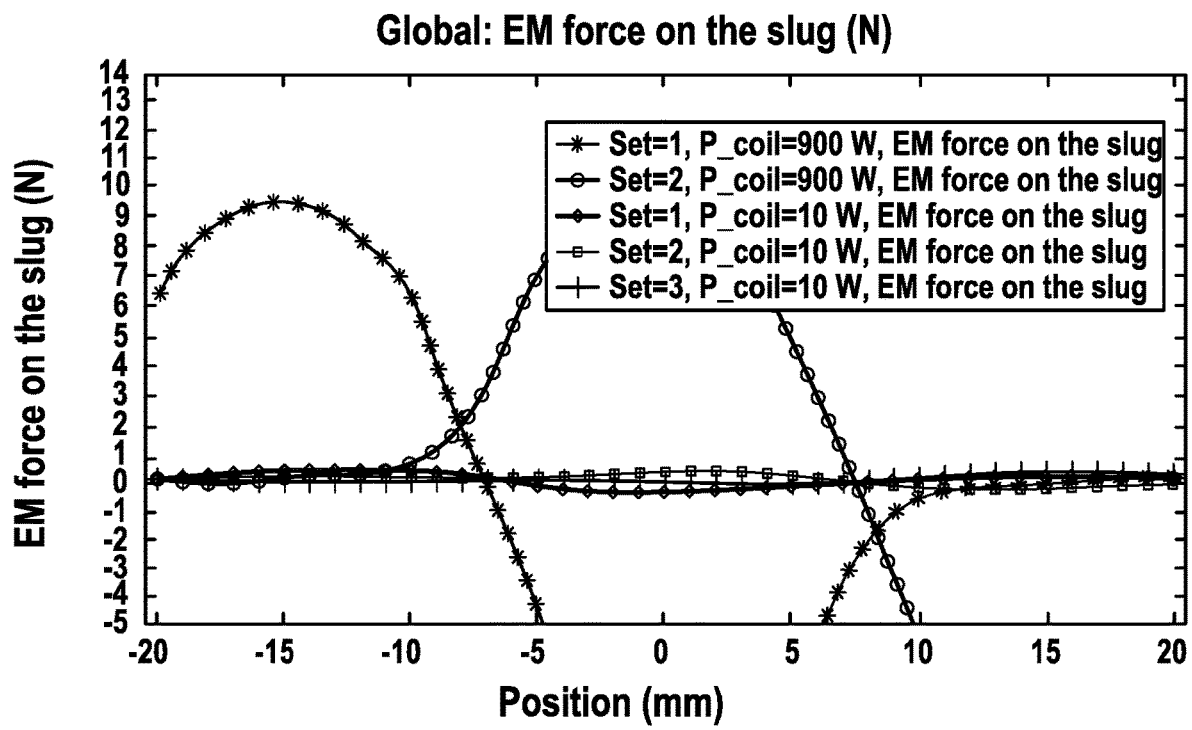
FIG. 28 shows a third set of force profiles for different active coil sets of the electromagnetic unit of the mixing unit of FIG. 17 in a diagram in which the electromagnetic force on the slug-like element is shown as a function of the axial position within the opening.
Figure 29:
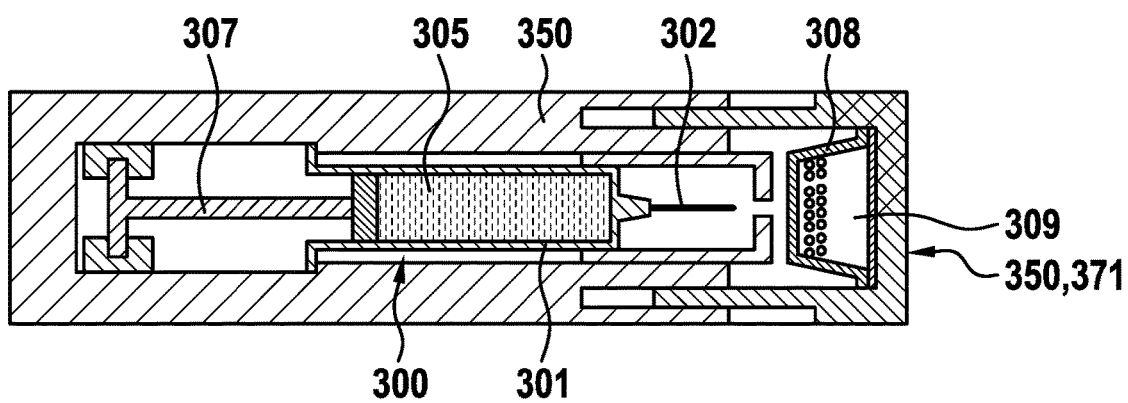
FIG. 29 shows an injection device and a detail of a base station of another embodiment of an inventive system in a longitudinal section as a concept sketch.

Instead of using a moving magnetic material for the electromagnetic element 210 (a "Lorentz force" device or linear brushless motor), the element 210 could made of a soft magnetic material, e.g. mild steel. In this case only one coil is needed to be activated at any time and the syringe works as a simple electromagnetic, e.g. a solenoid actuator. FIG. 28 shows that such an actuator generates even higher instantaneous forces for a given power input but these forces vary more with the position of the soft magnetic element within the first chamber 205 so that the coils must be carefully sized/placed to avoid positions of the element 210 in which no force is generated. If the element 210 is a soft magnetic material, it could be, for example, medical-grade stainless steel, in which case no coating is required. In that case, the magnetic element 210 may form sharp edges to more effectively puncture the foil.

In another embodiment instead of using a simple syringe, the injection device can be complete autoinjector. The above explained process may be conducted as indicated above: the autoinjector containing the first and second chambers comprising the first and second drug component is inserted into the base station, the components are mixed and the autoinjector is removed ready to use.

As a further embodiment, e.g. for high-value drugs, it may be economically viable to include the electromagnetic unit, the power supply and the control unit into a disposable component of the injection device so that no separate base station is needed.

In a further embodiment the internal shape of the needle 202, of the first chamber 205 and of the housing 201 of the syringe 200 may be designed such that the element 210 will not hinder injection should the element 210 remain in the first chamber 205 after mixing.

Rather than a syringe or an autoinjector, the injection device may be a cartridge suitable for use with a separate injection device. In other words, it is a syringe, but missing the long plunger that enables a user to carry out injection, and also missing the needle: the injection device includes the system for penetrating the skin, and also the system for driving injection.

The inventive system shown in FIGS. 16 to 28 comprising a syringe 200 and a base station 250 for drug reconstitution and/or mixing is extremely good operationally because there is no danger of contamination during the reconstitution process as it all occurs within a factory-sealed environment. The disposable part comprising the syringe 200 is very compact. The mixing/reconstitution is very predictable and consistent with a low amount of steps. There is only one disposable part per injection. The design of this base station offers maximum flexibility across injection device types namely pre-filled syringes, autoinjectors and cartridges. The injection device does not need a needle fitted in advance of reconstitution.

The embodiment of a drug reconstitution system shown in FIGS. 29 to 32 comprises a prefilled injection device in form of a syringe 300 with a housing 301 and a vial 308. The syringe 300 comprises a first chamber 305 which contains a first fluid drug component, for example a diluent. The vial 308 comprises a second chamber 309 containing a second solid and/or fluid drug component, for example a lyophilized drug. Additionally, the system comprises a supporting unit 310 which consists of, for example, two parts 310a and 310b (see FIG. 31) which may be releasable connected to each other, e.g., by means of a snap connection. The syringe 300 is further connected to a needle 302, wherein the needle 302 is covered by a needle boot 315. The syringe 300 further comprises a plunger 307 at its proximal end opposite from the distal end of the syringe 300 which is connected to the needle 302. The plunger 307 is movable within the housing 301 of the syringe 300 along an axial (longitudinal) direction of the syringe 300. The plunger 307 closes the proximal end of the first chamber 305. If the plunger 307 is moved in proximal direction an underpressure is generated within the first chamber 305. If the plunger 307 is moved in distal direction the first drug component is expelled from the first chamber 305 through the needle 302.

The drug reconstitution system further comprises a base station 350 comprising a housing 351 and, within the housing 351, at least one drive unit 370.

Figure 30:
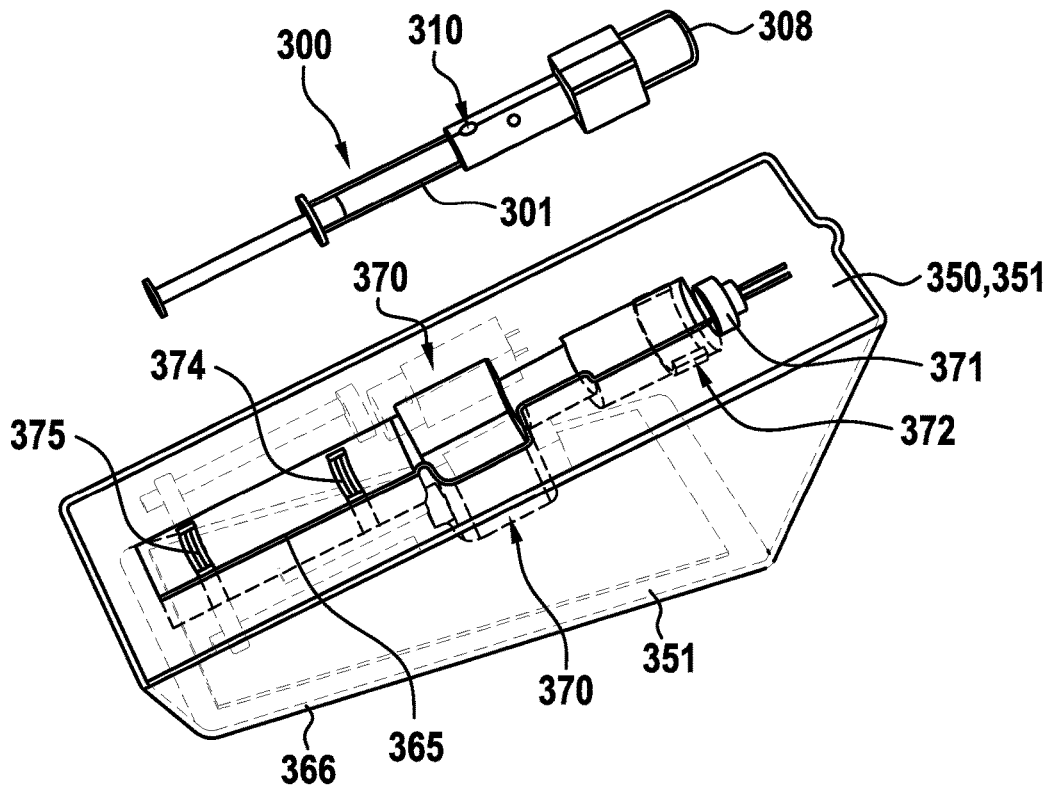
FIG. 30 shows another embodiment of an inventive system comprising an assembly with an injection device, a vial and a supporting unit as well as a base station in a perspective view from the side, wherein the base station is shown partially transparent.
Figure 31:
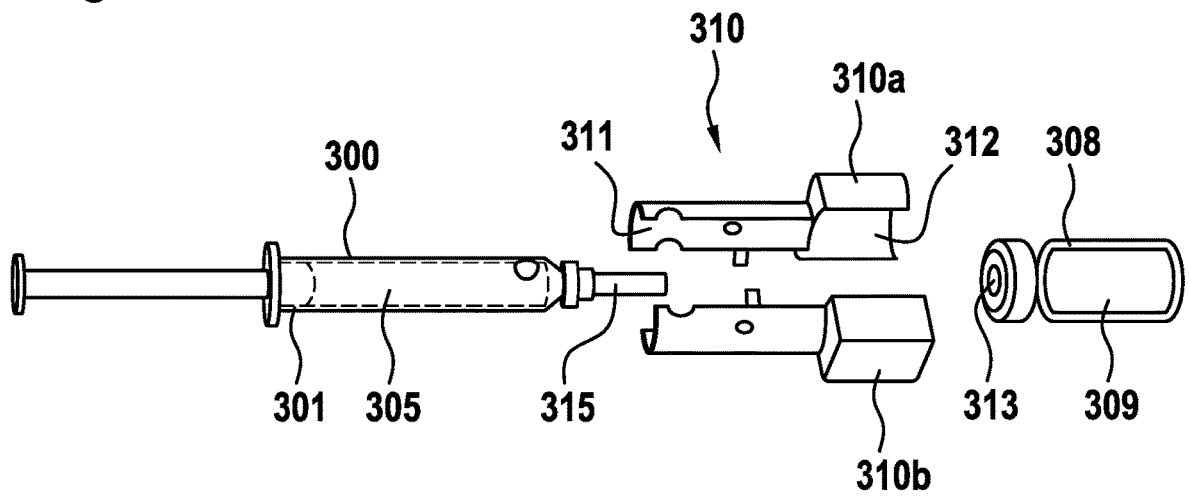
FIG. 31 shows the disposable subassembly from FIG. 30 in an exploded view from the side.

The supporting unit 310 is formed like a capsule or a hollow cylinder which comprises two sections with different diameter when both parts 310a, 310b shown in FIG. 31 are connected to each other (see FIG. 30). Alternatively, the connection of both parts 310a, 310b of the supporting unit 310 may be a hinge connection. The supporting unit 310 forms a first recess 311 and the second recess 312 on the inner side of each part 310a, 310b such that the supporting unit 310 locks the pre-filled syringe 300 and the vial 308 in a locked position during transit and storage, preventing them from making contact with each other. Therefore, the syringe 300 is fixed such in the first recess 311 and the vial 308 is fixed such in the second recess 312 that they have a predetermined distance from each other (see FIG. 32). For example the first recess 311 and the second recess 312 each may comprise at least one web or similar projection at its inner surface which forms a snap connection with the housing 301 of the syringe and/or the needle boot 315 or which forms a snap connection with the vial 308, for example at its neck section (see FIG. 32). If the syringe 300 and the vial 308 are fixed within the supporting unit 310 and both parts 310a and 310b of the supporting unit 310 are connected to each other, a self-supporting assembly is formed which locks the pre-filled syringe 300 and the vial 308 in position, for example, during transit and storage, preventing them from making contact with each other.

The vial 308 comprises a seal 313 which covers the vial 308 at its front end of the neck. The seal 313 closes the second chamber 309 hermetically.

The drive unit 370 of the base station 350 comprises for example a first motor and a second motor. Additionally, an optional high frequency transducer 371 as a vibrating unit and further an optional heater element 372 are provided within the housing 351 of the base station 350. The base station 350 further comprises a recess 365 at the upper side of the housing 351 which is adapted to receive and releasably fix the assembly comprising the syringe 300, and the vial 308 when locked within the supporting unit 310. Therefore the recess 365 at least partly corresponds to the outer circumference of the assembly.

Figure 32:
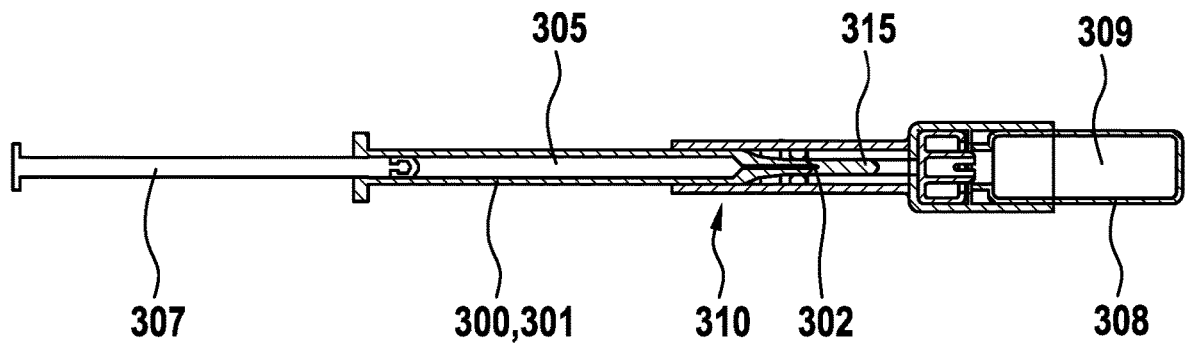
FIG. 32 shows the assembly of FIG. 31 prior fixing at the base station in a longitudinal section.

In order to reconstitute a drug and to prepare the syringe 300 for injection the assembly shown in FIG. 32 comprising the syringe 310, the supporting unit 310 and the vial 308 is inserted into the recess 365 of the base station 350 by the user and fixed there. The syringe 300 with the needle 302 and the vial 308 is now in the initial position. The base station 350 has the following interfaces to the assembly shown in FIG. 32:

- the vial, 308, is held stationary;
- the syringe 300 engages, for example with its housing 301, with a first linear slide 374 that is actuated in an axial direction by a motor drive unit 370;
- and plunger 307 engages with a second linear slide 375 that is actuated in an axial direction by a second, independent, motor drive unit (not shown).

The fixing of the assembly of FIG. 32 may be achieved either through:

- passive clips, which the user can overcome to pull the assembly out; or,
- a separate motor drive unit can operate a clamping mechanism to hold the assembly in place during the reconstitution process; or,
- the assembly shown in FIG. 32 can only engage/disengage with the first and second linear slides when they are in their initial positions.

In operation, in the position in which the assembly of FIG. 32 is inserted, that assembly may have to pass through slots in housing 351 that align with the first and second linear slides. Once the drive units have begun to move, features on the assembly no longer align with the slots in housing 351, and the user cannot remove the assembly prematurely. Thereby, the assembly is held at an angle in the base station 350 with the vial 308 positioned higher than the syringe 300 so that second component from the second chamber 309 of the vial 308 rather than air is drawn into the syringe 300 during preparation. This is realized by the tilting angle of the recess 365 of the base station 300 with regard to the opposite platform face 366 on which the base station 350 stands. The base station 350 contains a feature to unlock the parts of the supporting unit 310 allowing the syringe housing 301 and the vial 308 to move relative to each other when positioned within the recess 365 of the base station 350. For example, this unlock feature may consist of a flexible hook element inside supporting unit 310 which locks into a feature on the syringe housing 301, so that the two parts cannot move relative to each other. A pin feature in recess 365 may penetrate a small hole in supporting unit 310, to push the flexible hook element out of the way, enabling housing 301 to move relative to supporting unit 310. Alternatively, rather than being a fixed pin, this unlock feature could be actively driven, e.g. with a solenoid. The feature should remain unlocked as the assembly is removed from the base station 350, so that the user can withdraw the syringe 300 for injection.

In the next step the first motor of the drive unit 370 drives the housing 301 of the syringe 300 towards the vial 308 by means of the first slide 374. The needle boot 315 is compressed against the vial 308 and the needle 302 is inserted into the seal 313 of the vial 308 forming a fluid connection with the second chamber 309 of the vial 308. The syringe 300 with the needle 302 is moved toward the vial 308 and inserted into the second chamber 309 for a pre-defined distance. At the same time the second motor of the drive unit 370 moves the syringe plunger 307 by means of the second slide 375 towards the vial 308 at the same rate so that the volume inside the first chamber 305 stays unchanged during this step. The vial 308 and the syringe 300 with the needle 302 are now in an activated position.

In the next step, after the activated position of vial 308 and syringe 300 is reached, with the first motor held stationary, the second motor drives the syringe plunger 307 towards the vial 308 by means of the second slide 375, expelling the first drug component, for example the diluent, into the second chamber 309 of the vial 308 forming a mixture of the first drug component and the second drug component within the second chamber 309.

A range of mechanisms can be used to convert the rotational motion of the drive units 370 into a linear action on housing 301 of syringe 300 and plunger 307. The unit shown in FIG. 30 comprises a lead screw, where the motor of drive unit 370 turns a threaded bar. There is a nut running on the threaded bar, which is fixed both rotationally and axially to the first linear slide 374 that engages with housing 301 of syringe 300. As the threaded bar is rotated, the nut is driven along the threaded bar, driving housing 301 in an axial direction. The same may be provided by the second linear slide 375 coupled to plunger 307. Alternatively, the threaded bar can be fixed rotationally and axially to the profiled component engaging with 301 or 307, and the nut is driven rotationally by the motor. This nut can form part of the motor itself.

Once all first fluid drug component has been transferred into the second chamber 309, the transducer 371 may agitate the vial 308 containing the mixture of the first drug component and the second drug component, promoting mixing of, for example, the drug powder and the diluent. This transducer 371 may be a piezoelectric transducer, i.e. a piece of piezoelectric ceramic between two electrodes. If an oscillating voltage is applied to the electrodes, the thickness of the transducer oscillates, creating a pressure wave. Due to the inherently small displacements of piezoelectric transducers, very good acoustic coupling is necessary between the transducer 371 and the vial 308. This is likely to require at least a spring-loaded contact between the transducer and the vial, or even a liquid- or gel-based coupling. Alternatively, the transducer 371 may be an electromagnetic linear actuator, such as a voice coil or a solenoid. This operates at lower frequency, but the larger displacements achievable mean that it is simpler to transmit the agitation into the mixture. Alternatively, a motor driving an imbalanced load (a vibration motor) could be used to generate the oscillating pressure waves. At the same time or afterwards, the heater element 372 may heat up the mixture to a pre-set temperature, for example in the range of 18° C. to 26° C., reducing the likelihood that a cold mixture causes discomfort during drug injection into the patient. The heater element 372 may be a simple resistive element, generating heat when an electric current passes through. A thermistor (temperature measurement sensor) would be necessary to ensure that it is not overheated, unless the system is designed so that it is physically impossible for any fault to lead to overheating. Alternatively, heat can be supplied through a solid-state heat pump, i.e. a Peltier device.

Once the second drug component is fully dissolved in the first drug component or the other way around forming a reconstitution or once both components are mixed and—if applicable—the reconstitution or mixture reaches the correct temperature, the second motor drives the syringe plunger 307 by means of the second slide 375 into axial direction away from the vial 308 drawing the mixture or reconstitution into the syringe 300, namely from the second chamber 309 of the vial 308 into the first chamber 305 of the syringe 300. Since the vial 308 is positioned higher than the syringe 300, and the needle 302 is at the lowest point of the vial 308, the base station ensures that only the mixture or reconstitution of the second chamber 309 has drawn into the syringe 300, minimizing the air volume in the syringe 300. In the next step the first motor and the second motor of the drive unit 370 act together to pull the syringe 300 and with it the needle 302 out from the vial 308. The user then takes the syringe 300 out from the recess 365 of the base station 350, removes the supporting unit 310 from the syringe and manually injects the reconstituted or mixed drug contained in the first chamber 305 of the syringe 300. The vial 308 is a disposable device, wherein the syringe 300 may be a disposable or reusable device.

The embodiment of a drug mixing or reconstitution system shown in FIGS. 33 to 37 is similar to the embodiment shown in FIGS. 29 to 32 but with an autoinjector 400 instead of the syringe 300. An element of this embodiment of the system having the same last two digits of the reference number but a leading digit 4 instead of 3 corresponds to the respective element of the system shown in FIGS. 29 to 32.

The autoinjector 400 may be a traditional spring driven design or one that is actuated by a fluid, for example, air pressure. In the following, embodiments are explained by means of an autoinjector 400 actuated by air pressure which is provided to users with atmospheric pressure in an air chamber 414 initially. The embodiments works similarly with an autoinjector using a spring as the drug delivery energy source.

The drug reconstitution system comprises the autoinjector 400, a vial 408 and a supporting unit 410 which comprises two parts 410a and 410b for connecting to each other and fixing the autoinjector 400 and the vial 408 within forming an assembly for transit and storage in a pre-defined distance or relative position to each other. Additionally, a base station 450 is provided.

The autoinjector 400 further comprises a first chamber 405 and a needle 402. The first chamber 405 contains a first drug component, for example a diluent. The vial 408 comprises a second chamber 409 containing a second drug component, for example a lyophilized drug, and a seal 413 covering the vial and closing its second chamber 409 hermetically. The system comprises further a needle boot 415.

Figure 35:
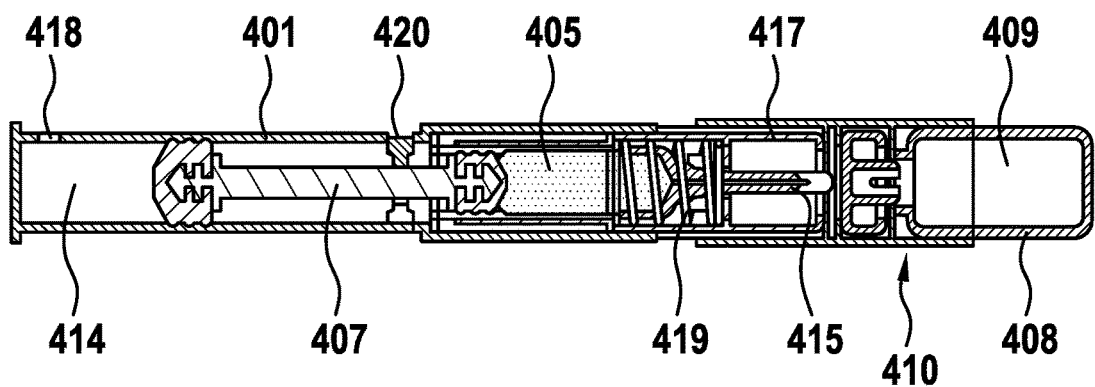
FIG. 35 shows the subassembly of FIG. 34 in a longitudinal section prior reconstitution.
Figure 36:
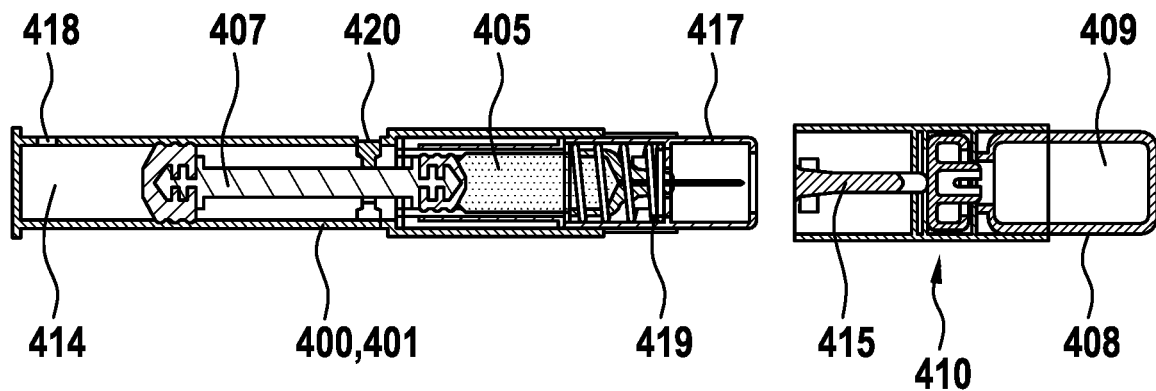
FIG. 36 shows the subassembly of FIG. 34 in a longitudinal section after reconstitution.

For reconstitution or mixing of the first and second drug components of the autoinjector 400 and the vial 408 the needle boot 415 is attached to a first recess 411 of the supporting unit 410 as shown in FIG. 36. Then, the assembly is composed by connecting the first and second part 410a, 410b of the supporting unit 410 to each other and inserting the vial 408 and the autoinjector 400 into their respective first and second recess 411, 412. For attachment of the autoinjector 400 to the supporting unit 410 a needle guard 417 of the autoinjector 400 has to be retracted in order to expose the needle 402 which is then covered by the needle boot 415 (see FIG. 35). The autoinjector 400 and the vial 408 are fixed to the supporting unit 410 for example by a snap connection.

Figure 33:
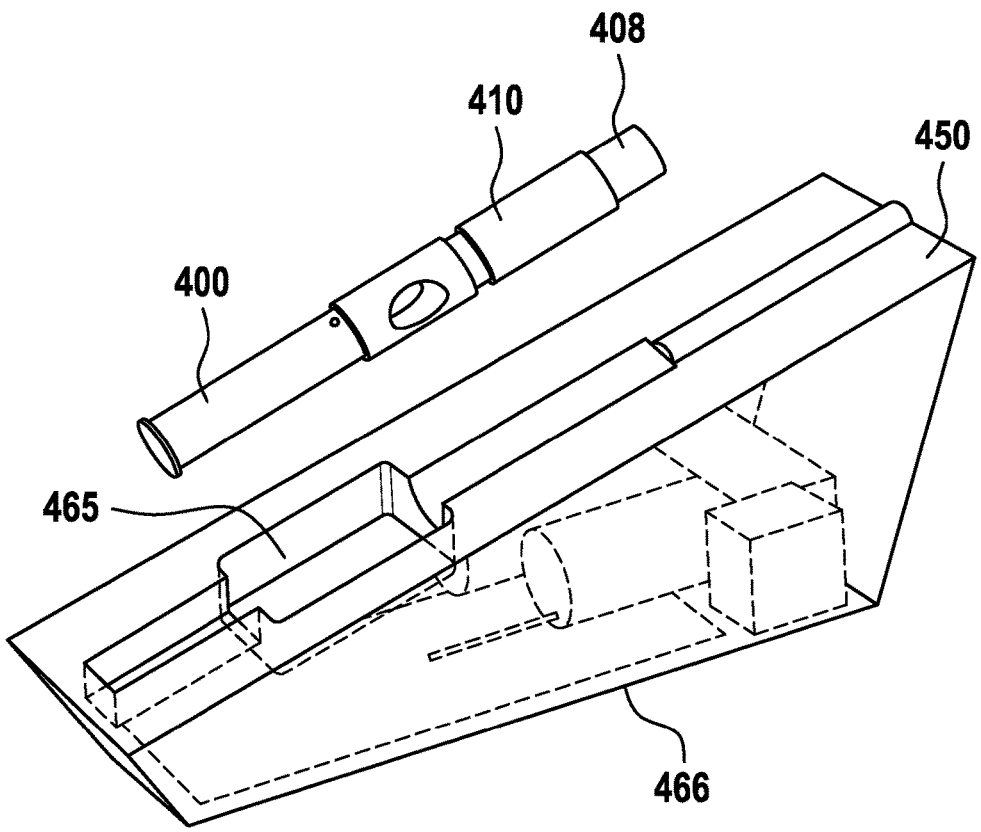
FIG. 33 shows another embodiment of an inventive system comprising an assembly with an injection device, a vial and a supporting unit as well as a base station in a perspective view from the side, wherein the base station is shown partially transparent.
Figure 34:
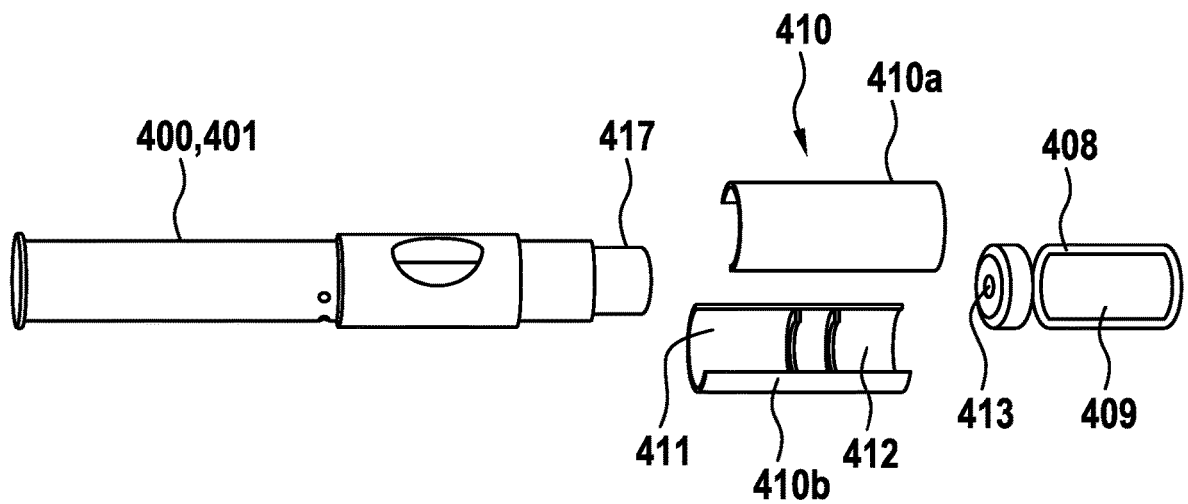
FIG. 34 shows the disposable subassembly from FIG. 33 in an exploded view from the side.

In order to reconstitute a drug with the system shown in FIGS. 33 to 37 the assembly (see FIG. 35) is inserted into a recess 465 of the base station 450 as shown in FIG. 33. Now the autoinjector 400 and the vial 408 are in an initial position. A feature on the base station 450 unlocks the parts 410a, 410b of the supporting unit 410, allowing the autoinjector 400 with the needle boot 415 and the vial 408 to move towards each other along an axial direction of the autoinjector 400 by means of a first slide connected to the drive unit 470. For example, the unlock feature may consist of a flexible hook element projecting from the inner surface of the supporting unit 410 which locks into a respective recess on outer surface of the autoinjector housing 401, so that the supporting unit 410 and the autoinjector housing 401 cannot move relative to each other. A pin feature in recess 465 may penetrate a small through hole in supporting unit 410 when correctly attached to the base station 450 within the recess 465, to push the flexible hook element out of the way, enabling autoinjector housing 401 to move relative to the supporting unit 410. Alternatively, rather than being a fixed pin, this unlock feature could be actively driven, e.g. with a solenoid, or a second drive motor. Alternatively, instead of activating a release mechanism inside supporting unit 410, the unlock feature could fully open supporting unit 410 up, i.e. separate the two parts 410a, 410b of the autoinjector housing. The unlock feature should remain unlocked as the assembly is removed from the base station 450, so that the user can withdraw the syringe 400 for injection.

Figure 37:
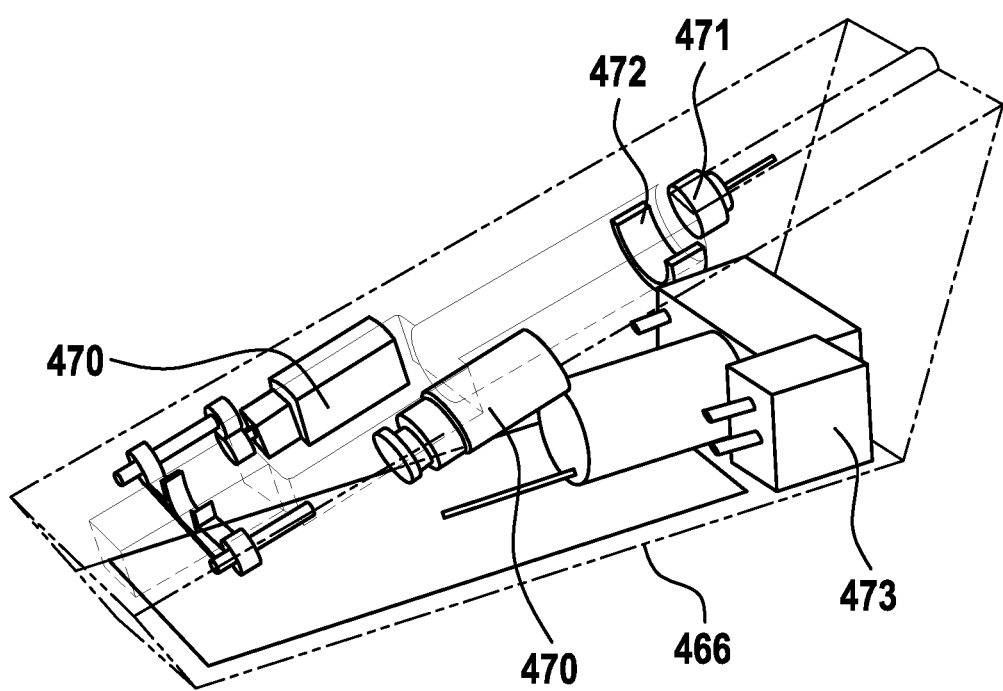
FIG. 37 shows the base station of FIG. 33 in a perspective view from the side, partially transparent.

In the next step, a needle of the base station 450 pierces a septum 418 at the autoinjector body 401, allowing an air pump 473 of the base station 450 to pump air in and out an autoinjector air chamber 414 comprising the plunger 407. The needle is fluidly connected to the air pump 473. Then, a first motor of a drive unit 470 of the base station 450 pushes the autoinjector 400 towards the vial 408. Thereby the needle guard 417 retracts further into the autoinjector body 401 and the needle boot 415 is compressed so that the needle 402 is inserted into the vial 408, e.g. its second chamber 409, through the seal 413 for example formed as a rubber cap. The first slide connected with the drive unit 470 engages with a feature on housing 401, and drives it axially. A range of mechanisms can be used to convert the rotational motion of the drive unit motor into a linear action on the autoinjector body 401. The mechanism shown in FIG. 37 is a lead screw, where the motor turns a threaded bar. There is a nut running on the threaded bar, which is fixed both rotationally and axially to a first linear slide (e.g. a profiled component) that engages with the autoinjector body 401. As the threaded bar is rotated, the slide is driven along the threaded bar, driving autoinjector body 401 in an axial direction towards the vial 408 thereby inserting the needle 402 into the second chamber 409. The autoinjector 400 and the vial 408 are now in an activated position.

Afterwards, a second motor of the drive unit 470 of the base station 450 activates a mechanism of the autoinjector 400 to unlock a plunger 407 of the autoinjector 400 allowing the plunger 407 to move using a plunger locking mechanism 420. The locking mechanism 420 exists so that once the autoinjector 400 is filled and primed, it does not release its stored energy and inject drug until it is activated by the user. It is shown in FIG. 35 as a simple locking pin, but it can be any catch feature that locks the plunger in position. This catch is later released to initiate drug delivery, e.g. the user presses a button to move the catch away from the plunger, or the catch is released when the needle guard is pressed against the skin. However, it must also be operated by the base station 450, in order that the base station 450 can perform mixing and priming of the autoinjector 400. Therefore, second motor of the drive unit 470 releases the autoinjector plunger 407, for example by releasing the catch of the locking mechanism 420. Then, driven by the drive unit 470, the air pump 473 of the base station 450 pumps air into the air chamber 414 surrounding the plunger 407 via the needle which pierces the septum 418 thereby pushing the plunger 407 towards the vial 408 to expel the first drug component from the first chamber 405 at the same time.

Accordingly, the first drug component of the first chamber 405 can now be mixed and/or reconstituted within the second chamber 409 of the vial 408 with the second drug component.

For mixing and/or reconstituting, the base station 450 may vibrate the vial 408 at a high frequency using a transducer 471 (vibrating unit) and/or warm up the mixture within the vial 408 at the same time using a heater element 472. Once the mixture or reconstitution is prepared, the air pump 473 of the base station 450 works in reverse to pump air out of the air chamber 414 generating a vacuum in order to pull the plunger 407 away from the vial 408 such that the drug mixture or reconstitution is drawn into the first chamber 405 of the autoinjector 400. In the next step the second motor of the drive unit 470 activates the plunger locking mechanism 420 to lock the plunger 407 in position again. Now, the air pump 473 pumps compressed air into the air chamber 414, this time as the drug delivery power source. Then the first motor draws the autoinjector 400 out of the vial 408, allowing the user to remove the assembly 410 from the base station 450.

In order to use the autoinjector 400, the user pulls to remove the vial 408 and the supporting unit 410 by opening the two parts 410*a*, 410*b*. This also removes the needle boot 415 from the autoinjector 400 in the same step. Removal of the needle boot 415 has the additional advantage that it removes the chance of injecting rubber debris from the needle boot 415 into the patient. This step also reveals the needle guard 417 (see FIG. 36). Then, the user presses the needle guard 417 onto the injection site, pushing the needle guard 417 into the autoinjector body 401 and inserting the needle 402 into the patient. A feature of the needle guard 417 activates the mechanism of the autoinjector 400 to unlock the plunger 407. In one embodiment of the unlock mechanism there is an axial extension of needle guard 417 towards the locking mechanism 420. As the needle guard 417 is pushed back into housing 401, this extension engages with a ramp or similar mating feature in locking mechanism 420, moving it out of the plunger 407 or otherwise disengaging the locking mechanism. The plunger 407 then moves towards the needle 402 under air pressure thereby providing injection of the mixture or reconstitution into the patient. Once the injection is finished, the user removes the autoinjector 400 from the injection site and the needle guard 417 extends outwards under a spring force of a spring 419 to cover the needle 402 again. The needle guard 417 also locks itself against the autoinjector body 401 to prevent needle 402 stick injuries.

In an alternative embodiment of the above explained autoinjector concept actuated by air pressure an autoinjector concept using a spring as the drug delivery energy source can be used. The inventive method is basically the same except for during the mixing and/or reconstitution stage the second motor of the drive unit 470 actuates the plunger 407 to expel the first drug component into the second chamber 409 of the vial 408. After mixing or reconstitution, the second motor withdraws the plunger 407, producing an underpressure within the first chamber 405 and drawing the mixed or reconstituted drug into the autoinjector 400, namely its first chamber 405. Completion of this movement happens when the plunger 407 reaches its locking position at the proximal end, wherein this action may compress a delivery spring ready for drug delivery at the same time. Activation happens analogously to the above embodiment, when the user presses the needle guard 417 onto the injection site, pushing the needle guard 417 into the autoinjector body 401, inserting the needle 402 into the patient and unlocking the plunger 407, allowing the spring to drive the plunger 407 downwards to expel the drug from the first chamber 405. Although the above example states compressing the delivery spring when drawing the drug back into the autoinjector 400 it is also possible for the spring to be compressed during manufacturing.

In a further alternative embodiment the mixture comprising the first drug component and the second drug component can be transferred back and forth between the first chamber 305, 405 of the autoinjector or syringe and the second chamber 309, 409 of the vial 308, 408. Thereby, the respective needle 302, 402 preferably creates water jet during transfer, promoting mixing or reconstitution.

Before the user injects the mixed or reconstituted drug the user may prime the syringe 300 manually. In another embodiment instead of priming the syringe 300 manually, the base station can be provided with a respective feature to prime the syringe 300. This can be done, for example, by using the second drive mechanism which axially moves the plunger 307 a small distance, whilst holding housing 301 still, so that any air in the syringe is expelled. The same applies to the autoinjector 400, wherein the autoinjector may either be powered by air pressure or a conventional mechanical spring.

The main advantage of the above described inventive drug reconstitution system with a base station 350, 450, a syringe 300 or autoinjector 400, a supporting unit 310, 410 and a vial 308, 408 consists therein, that it automates the reconstitution operation, thereby removing all manual steps. If a transducer 371, 471 is provided in the base station 350, 450 it improves the consistency and repeatability of reconstitution. The system further reduces the number of devices presented to the user and removes the need to disinfect the drug vial 308, 408. Additionally, it reduces the chance of injecting air into the patient. With regard to the autoinjector version, wherein the base station 450 primes the autoinjector 400 right before use there is the advantage that this allows the autoinjector 400 to be stored and transported without stress, reducing the complexity of the autoinjector 400 and the risk of misfire and failure.

REFERENCE NUMBERS 100, 200, 300, 500 syringe
101, 201, 301, 351, 501, 510*a* housing
101*a* ratchet
101*b* return track
102, 202, 302, 402, 502 needle
105, 205, 305, 405, 505 first chamber
107, 207, 307, 407, 507 plunger
107*a* clip member
108 distal end section
109, 209, 309, 409, 509 second chamber
111, 511 lower piston
112, 512 upper piston
112*a* clip member
113 handle
114 through hole
115, 315, 415 needle boot
117 cotter pin
120 rib
122 needle
125 membrane
210 slug-like element
210*a* distal end
210*b* proximal end
211, 313, 413 seal 213 arrow
214 arrow
215 needle cover
220 element
250, 350, 450 base station
260 electromagnetic unit
260a electromagnetic coil
260b steel pole piece
262 line of magnetic field
265 opening
270 control unit
275 button
308, 408 vial
310, 410 supporting unit
310a, 310b, 410a, 410b part of supporting unit
311, 411 first recess
312, 412 second recess
365, 465, 511a recess
366, 466 platform face
370, 470 drive unit
371, 471 transducer
372, 472 heater element
374 first linear slide
375 second linear slide
400 autoinjector
401 autoinjector body
414 air chamber
417 needle guard
418 septum
419 spring
420 locking mechanism
473 air pump
513 projection
530 compression spring
535 cap
536 clip mechanism
538 O-ring
540, 541, 542 arrow

The invention claimed is:

1. A device comprising:
a first material within a first chamber;
a housing; and
a plunger comprising a second chamber comprising a second material and a movable element with an electric, magnetic, or paramagnetic characteristic,
wherein one of the first material and the second material is a fluid,
wherein the second chamber is initially closed,
wherein the movable element, the first chamber, and the second chamber are adapted such that after activation by an electromagnetic field, the movable element moves in a pre-determined direction of the device and thereby opens a path providing a fluid communication between the first chamber and the second chamber.

2. The device according to claim 1, wherein the movable element is a slug-like element and comprises a tip at a distal end.

3. The device according to claim 2, wherein the movable element comprises a tapered face at a proximal end.

4. The device according to claim 1, wherein the slug-like element comprises a permanent magnetic material or a soft magnetic material.

5. The device according to claim 1, further comprising a filter at a distal end of the first chamber (205).

6. The device according to claim 5, further comprising a seal that is adapted such that the seal does not produce a shard when punctured or ruptured by the slug-like element.

7. The device according to claim 1, wherein the plunger comprises a plate-like element comprising a soft magnetic material accommodated proximally with regard to the second chamber.

8. A system comprising:
a device comprising:
a first material within a first chamber,
a housing, and
a plunger comprising a second chamber comprising a second material and a movable element with an electric, magnetic, or paramagnetic characteristic,
wherein one of the first material and the second material is a fluid,
wherein the second chamber is initially closed, and
wherein the movable element, the first chamber, and the second chamber are adapted such that after activation by an electromagnetic field, the movable element moves in a pre-determined direction of the device and thereby opens a path providing a fluid communication between the first chamber and the second chamber; and
a base unit comprising:
a recess for accommodating the device,
a control unit, and
an electromagnetic unit that is adapted to produce an electromagnetic field that penetrates the recess,
wherein the control unit electrically operates the electromagnetic unit, and
wherein the base unit is adapted such that after accommodating the device within the recess and after user activation of the base unit, the control unit operates the electromagnetic unit such that the movable element contained in the second chamber moves in a direction of the device determined by the electromagnetic field and thereby opens the path providing the fluid communication between the first chamber and the second chamber.

9. The system according to claim 8, wherein the electromagnetic unit comprises at least one electromagnetic coil surrounding the recess for the device.

10. The system according to claim 9, wherein the electromagnetic unit comprises a series of electromagnetic coils and milled steel pole pieces in between two adjacent electromagnetic coils.

11. The system according to claim 10, wherein the control unit is adapted to energize electromagnetic coils such that the electromagnetic field moves the movable element back and forth along the pre-determined direction of the device.

12. The system according to claim 8, wherein the electromagnetic unit comprises at least one permanent magnet that is moveable along the pre-determined direction of the device.

13. The system according to claim 8, wherein the movable element is a slug-like element and comprises a tip at a distal end.

14. The system according to claim 13, wherein the movable element comprises a tapered face at a proximal end.

15. The system according to claim 8, wherein the slug-like element comprises a permanent magnetic material or a soft magnetic material.

16. The system according to claim 8, wherein the device further comprises a filter at a distal end of the first chamber.

17. The system according to claim 8, wherein the plunger comprises a plate-like element comprising a soft magnetic material accommodated proximally with regard to the second chamber.

18. A method comprising:
accommodating a device within a recess of a base unit; the device comprising:
- a first material within a first chamber,
- a housing, and
- a plunger comprising a second chamber comprising a second material and a movable element with an electric, magnetic, or paramagnetic characteristic,
- wherein one of the first material and the second material is a fluid,
- wherein the second chamber is initially closed,
- wherein the base unit comprises an electromagnetic unit that is adapted to produce an electromagnetic field that penetrates the recess; and operating the electromagnetic unit by a control unit after activation such that the movable element within the second chamber of the device moves in a direction of the device determined by the electromagnetic field and thereby opens a path providing a fluid communication between the first chamber and the second chamber.

19. The method according to claim 18, wherein the electromagnetic unit is operated such that the electromagnetic field moves the movable element back and forth along a pre-defined direction of the device.

20. The method according to claim 18, wherein the electromagnetic unit is operated such that at least one permanent magnet of the electromagnetic unit moves along a pre-defined direction of the device after activation.

* * * * *